(12) United States Patent
Mehta et al.

(10) Patent No.: US 11,197,785 B2
(45) Date of Patent: Dec. 14, 2021

(54) WEARABLE DEVICE

(71) Applicant: Smardii, Inc., Miami, FL (US)

(72) Inventors: Vikram S. Mehta, Wayne, NJ (US);
Sebastien Gaddini, Cooper City, FL (US); Mathieu Gaddini, Le Pradet (FR)

(73) Assignee: SMARDII, INC., Miami, FL (US)

( * ) Notice: Subject to any disclaimer, the term of this patent is extended or adjusted under 35 U.S.C. 154(b) by 0 days.

(21) Appl. No.: 17/172,995

(22) Filed: Feb. 10, 2021

(65) Prior Publication Data

US 2021/0205150 A1 Jul. 8, 2021

Related U.S. Application Data

(63) Continuation of application No. PCT/US2020/067525, filed on Dec. 30, 2020.

(60) Provisional application No. 62/957,043, filed on Jan. 3, 2020.

(51) Int. Cl.
*A61F 13/42* (2006.01)
*A61F 13/15* (2006.01)

(52) U.S. Cl.
CPC ...... *A61F 13/42* (2013.01); *A61F 2013/1513* (2013.01); *A61F 2013/424* (2013.01)

(58) Field of Classification Search
CPC ............. A61F 13/42; A61F 2013/1513; A61F 2013/424; A61B 5/6808
See application file for complete search history.

(56) References Cited

U.S. PATENT DOCUMENTS

| 6,559,772 B2 | 5/2003 | Zand et al. |
| 7,755,497 B2 * | 7/2010 | Wada ...................... A61F 5/451 340/604 |

(Continued)

FOREIGN PATENT DOCUMENTS

| CA | 2992409 A1 | 1/2017 |
| CN | 106176054 A | 12/2016 |

(Continued)

OTHER PUBLICATIONS

International Preliminary Report on Patentability, dated Mar. 10, 2020, for PCT Application No. PCT/US2018/049793, 18 pages.

(Continued)

*Primary Examiner* — Catharine L Anderson
(74) *Attorney, Agent, or Firm* — Morrison & Foerster LLP

(57) ABSTRACT

The present disclosure relates generally to a wearable device, and more specifically to a wearable device for detecting biological events, monitoring health condition of an individual, and for providing automatic alerts and analytics reporting. An exemplary wearable device for monitoring health condition of an individual comprises a puck component attachable to the individual's clothing, wherein the puck component comprises a circuit of a moisture sensor; a strip component configured to be placed within the individual's clothing, wherein a proximal end portion of the strip comprises a pair of conductive pads, and wherein the pair of conductive pads is configured to interface with the circuit of the moisture sensor while the proximal end portion of the strip is enclosed within the puck via a coupling mechanism.

18 Claims, 21 Drawing Sheets

(56) References Cited

U.S. PATENT DOCUMENTS

| | | | |
|---|---|---|---|
| 8,698,641 B2* | 4/2014 | Abraham | A61F 13/84 340/604 |
| 8,975,465 B2* | 3/2015 | Hong | A61F 13/42 604/361 |
| 9,224,102 B2 | 12/2015 | Barda et al. | |
| 9,937,081 B2 | 4/2018 | Zand | |
| 10,335,326 B2* | 7/2019 | Wu | A61B 5/01 |
| 10,478,349 B2* | 11/2019 | Mancini | A61F 13/42 |
| 10,722,405 B2* | 7/2020 | Pepin | A61F 13/42 |
| 2007/0179356 A1 | 8/2007 | Wessel | |
| 2007/0270774 A1 | 11/2007 | Bergman et al. | |
| 2008/0167572 A1 | 7/2008 | Stivoric | |
| 2012/0109087 A1 | 5/2012 | Abraham et al. | |
| 2014/0200538 A1 | 7/2014 | Euliano | |
| 2015/0042489 A1 | 2/2015 | Lavon | |
| 2015/0180355 A1 | 6/2015 | Freeman | |
| 2016/0029957 A1 | 2/2016 | Faybishenko et al. | |
| 2016/0095758 A1 | 4/2016 | Haire | |
| 2017/0065464 A1 | 3/2017 | Heil et al. | |
| 2018/0011080 A1 | 1/2018 | Xu | |
| 2018/0177644 A1* | 6/2018 | Tuli | A61F 13/15756 |
| 2020/0222002 A1 | 7/2020 | Mehta | |

FOREIGN PATENT DOCUMENTS

| | | |
|---|---|---|
| EP | 2803342 A1 | 11/2014 |
| WO | 2013013197 A1 | 1/2013 |
| WO | 2016207799 A1 | 12/2016 |
| WO | 2019051118 A1 | 3/2019 |

OTHER PUBLICATIONS

International Search Report and Written Opinion, dated Jan. 7, 2019, for PCT Application No. PCT/US2018/049793, 26 pages.

International Search Report and Written Opinion, dated Apr. 29, 2021, for PCT Application No. PCT/US2020/067525, 11 pages.

Invitation to Pay Additional Fees, dated Mar. 3, 2021, for PCT Application No. PCT/US2020/067525, filed Dec. 30, 2020, 3 pages.

\* cited by examiner

FIG. 2C

Smardii     ⊞ DASHBOARD   @ANN PERKINS

Geriatrics Center | Floor 12    ← 292

ROOM B301    Dry   1h 44m
- Judy Breckenridge
- 39-J4037211
- Standing | 6 min
- 98.5° F
- ⚠ Heart surgery recovery
- ⊕ Biometrics   ⤺ History

ROOM B302    Wet   7 min
- Martha Evans
- 39-J400021
- Lying (back) | 1h 42m
- 96.5° F
- ⚠ —
- ⊕ Biometrics   ⤺ History

ROOM B303
+ ADD

ROOM B304    Dry   28 min
- Henry Moreau
- 39-J403298
- Walking | 2min
- 97.9° F
- ⚠ Vascular dementia
- ⊕ Biometrics   ⤺ History

ROOM B305   294   Dry   1h 31m
- Martha Kensington
- 39-J400021
- Lying (Side) | 1h 42m
- 98.2° F
- ⚠ Must be moved every hr
- ⊕ Biometrics   ⤺ History

ROOM B306    Dry   21 min
- Patricia Thamos
- 39-J4480012
- Sitting | 1h 52m
- 97.1° F
- ⚠ —
- ⊕ Biometrics   ⤺ History

ROOM B307    Dry   1h 6m
- Tom Haverford
- 39-J401094
- Lying (back) | 37m
- 98.6° F
- ⚠ —
- ⊕ Biometrics   ⤺ History

ROOM B308

✕ Mr. Stuart needs to be changed.   7 min
Room B302

✕ Ms. Kensington needs to be changed.   4 min   296
Room B305

Contact    Privacy Policy

© Smardii Inc. All rights reserved.

FIG. 2D

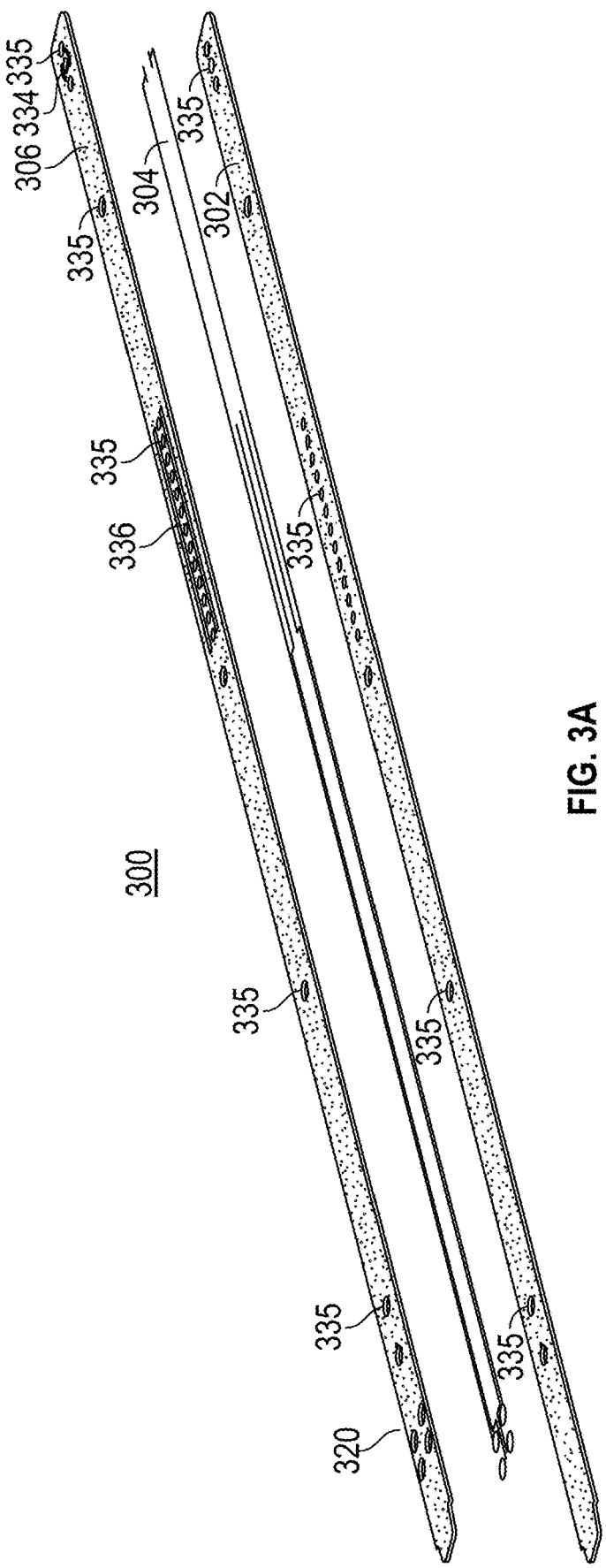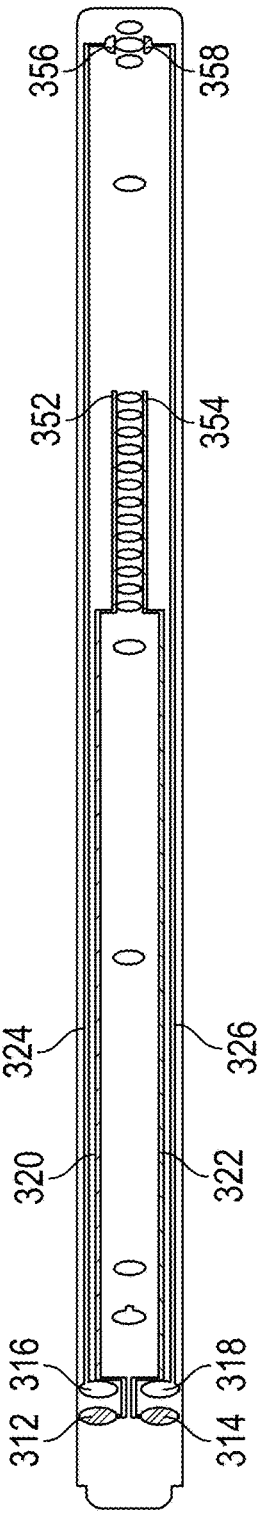
FIG. 3A
FIG. 3B

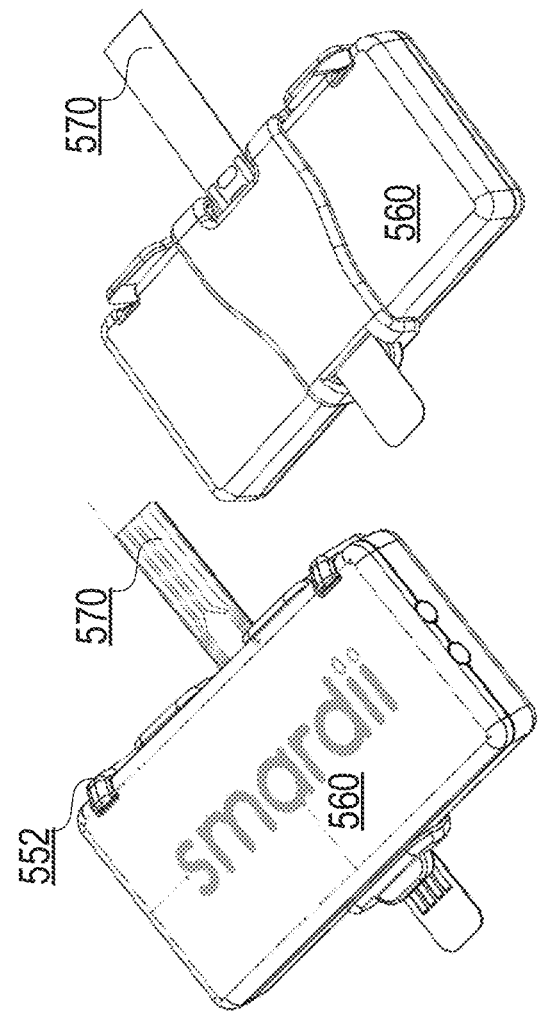
FIG. 5C   FIG. 5D   FIG. 5E

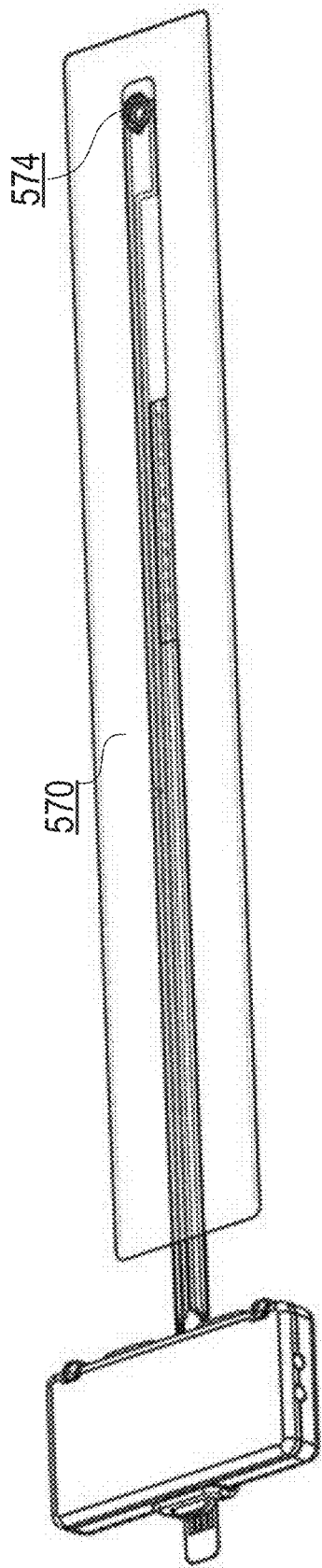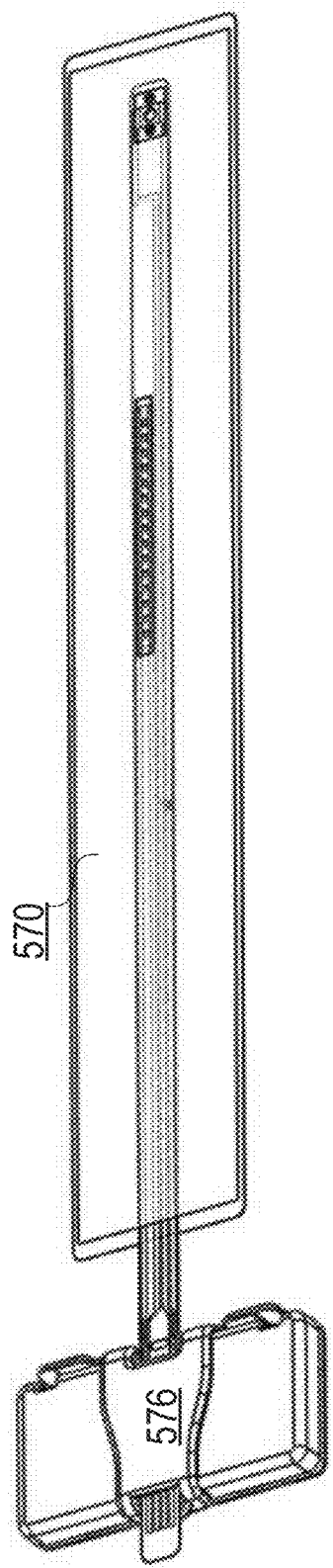
FIG. 5F
FIG. 5G

600

602
RECEIVING A FIRST PLURALITY OF MOISTURE MEASUREMENTS

604
IDENTIFYING A RISE OF MOISTURE LEVEL WITHIN A FIRST PREDEFINED THRESHOLD BASED ON THE PLURALITY OF MOISTURE MEASUREMENTS

606
RECEIVING A SECOND PLURALITY OF MOISTURE MEASUREMENTS TAKEN AFTER THE FIRST PLURALITY OF MOISTURE MEASUREMENTS

608
DETERMINING WHETHER THERE IS A DROP OF MOISTURE LEVEL MEETING A SECOND PREDEFINED THRESHOLD BASED ON THE SECOND PLURALITY OF MOISTURE MEASUREMENTS

610
IN ACCORDANCE WITH A DETERMINATION THAT THERE IS THE DROP OF MOISTURE LEVEL, IDENTIFYING A FIRST EVENT TYPE

612
IN ACCORDANCE WITH A DETERMINATION THAT THERE IS NOT THE DROP OF MOISTURE LEVEL MEETING THE PREDEFINED REQUIREMENT, IDENTIFYING A SECOND EVENT TYPE

FIG. 6A

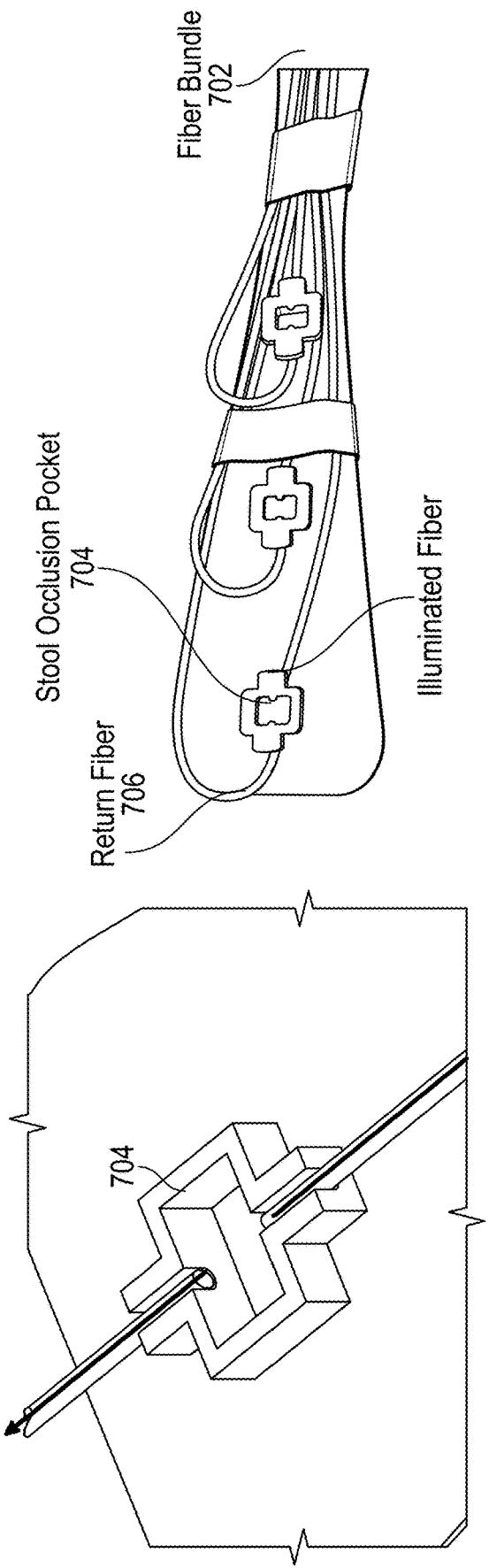

WEARABLE DEVICE

CROSS-REFERENCE TO RELATED APPLICATION

This application claims the benefit of U.S. Provisional Application 62/957,043, filed on Jan. 3, 2020, the entire contents of which are incorporated herein by reference for all purposes.

FIELD OF INVENTION

The present disclosure relates generally to a wearable device, and more specifically to a wearable device for detecting biological events, for monitoring health condition of an individual, and for providing automatic alerts and analytics reporting.

BACKGROUND

The world's elderly population continues to grow at an unprecedented rate. Maintaining the quality of life for the elderly is difficult and costly. For example, regular and consistent monitoring of many elderly individuals are required, both to detect incidents (e.g., urination, defecation, falling) that need to be quickly responded to and to observe the long-term health trend (e.g., sleeping patterns, temperature and other biometrics) of the individuals. However, such monitoring can be intrusive and cumbersome to the elderly individuals. Further, such monitoring require significant operational cost and manpower. This challenge is further exacerbated by the shortage of nurses and medical staff.

BRIEF SUMMARY

An exemplary method of monitoring a biological event associated with an individual comprises: receiving a first plurality of moisture measurements; identifying a rise of moisture level within a first predefined threshold based on the plurality of moisture measurements; receiving a second plurality of moisture measurements taken after the first plurality of moisture measurements; determining whether there is a drop of moisture level meeting a second predefined threshold based on the second plurality of moisture measurements; in accordance with a determination that there is the drop of moisture level, identifying a first event type; in accordance with a determination that there is not the drop of moisture level meeting the predefined requirement, identifying a second event type.

In some embodiments, the method further comprises automatically causing an alert based on an identified event type.

In some embodiments, the first event type is excretion of bodily fluid.

In some embodiments, the bodily fluid is urine or blood.

In some embodiments, the second event type is excretion of stool.

In some embodiments, determining whether there is a drop of moisture level meeting a second predefined threshold comprises: identifying the rise and the drop have occurred within a predefined time period.

In some embodiments, determining whether there is a drop of moisture level meeting a second predefined threshold comprises: calculating a rate of drop of moisture level.

An exemplary wearable device for monitoring health condition of an individual comprises a puck component attachable to the individual's clothing, wherein the puck component comprises a circuit of a moisture sensor; a strip component configured to be placed within the individual's clothing, wherein a proximal end portion of the strip comprises a pair of conductive pads, and wherein the pair of conductive pads is configured to interface with the circuit of the moisture sensor while the proximal end portion of the strip is enclosed within the puck via a coupling mechanism.

In some embodiments, the puck component comprises a main housing, and wherein the outer surface of the main housing exposes a pair of electrodes corresponding to the circuit of the moisture sensor.

In some embodiments, the puck component comprises a cradle attachable to the main housing to enclose the proximal end portion of the strip.

In some embodiments, the cradle comprises a buckle.

In some embodiments, the strip component comprises a flexible circuit, a spacer, and/or one or more holes.

An exemplary wearable device for monitoring health condition of an individual comprises: a strip component comprising: a first pair of proximal conductive pads located on a proximal end portion of the strip; a first pair of distal conductive pads connected to the first pair of proximal conductive pads via one or more conductive tracks, wherein the first pair of proximal conductive pads and the first pair of proximal conductive pads are configured to detect a first event type; a second pair of proximal conductive pads located on a proximal end portion of the strip; a second pair of distal conductive pads connected to the first pair of proximal conductive pads via one or more conductive tracks, wherein the second pair of proximal conductive pads and the second pair of proximal conductive pads are configured to detect a first event type.

In some embodiments, the first event type is excretion of bodily fluid.

In some embodiments, the second event type is excretion of stool.

An exemplary wearable device for monitoring health condition of an individual, comprises: a strip component comprising a pair of conductive pads, wherein a gap is formed between the pair of conductive pads; a top sheet placed over the strip component, wherein the top sheet comprises a hole for exposing the pair of conductive pads; a spacer comprising a ring portion and two supports, wherein the ring portion is placed over the top sheet and comprises a hole for exposing the pair of conductive pads, and wherein the supports hold the top sheet and the strip component to create spacing between the top of the ring portion and the pair of conductive pads.

In some embodiments, the pair of conductive pads are located at a distal portion of the strip.

In some embodiments, the strip comprises a flexible circuit.

An exemplary system monitoring health condition of an individual, comprises a strip component configured to be placed within the individual's clothing, wherein the strip component comprises: a gap configured to receive bodily waste, a first fiber configured to emit light across the gap, and a second fiber configured to receive the light emitted across the gap; a puck component attachable to the individual's clothing, wherein the puck component comprises a light-dependent resistor sensor, wherein the resistor sensor is connected to the first fiber and the second fiber.

In some embodiments, the resistor sensor comprises a photocell.

DESCRIPTION OF THE FIGURES

The patent application file contains at least one drawing executed in color. Copies of this patent or patent application publication with color drawings will be provided by the office upon request and payment of the necessary fee.

For a better understanding of the various described embodiments, reference should be made to the Description of Embodiments below, in conjunction with the following drawings in which like reference numerals refer to corresponding parts throughout the figures.

FIG. 2C illustrates an exemplary user interface of a software application, according to some embodiments.

FIG. 2D illustrates an exemplary user interface of a software application, according to some embodiments.

FIG. 3A illustrates an exemplary exploded view of a flexible circuit component within a strip component of a wearable device, according to some embodiments.

FIG. 3B illustrates an exemplary top view of a flexible circuit component, according to some embodiments.

FIG. 5C illustrates an exemplary cradle, according to some embodiments.

FIG. 5D illustrates an exemplary assembled wearable device, according to some embodiments.

FIG. 5E illustrates an exemplary assembled wearable device, according to some embodiments.

FIG. 5F illustrates an exemplary assembled wearable device, according to some embodiments.

FIG. 5G illustrates an exemplary assembled wearable device, according to some embodiments.

FIG. 6A illustrates an exemplary process of monitoring a biological event associated with an individual, according to some embodiments.

FIG. 7A illustrates operation of an exemplary fiber optical sensor, according to some embodiments.

FIG. 7B illustrates an exemplary fiber optical sensor, according to some embodiments.

DETAILED DESCRIPTION

Figure 1:
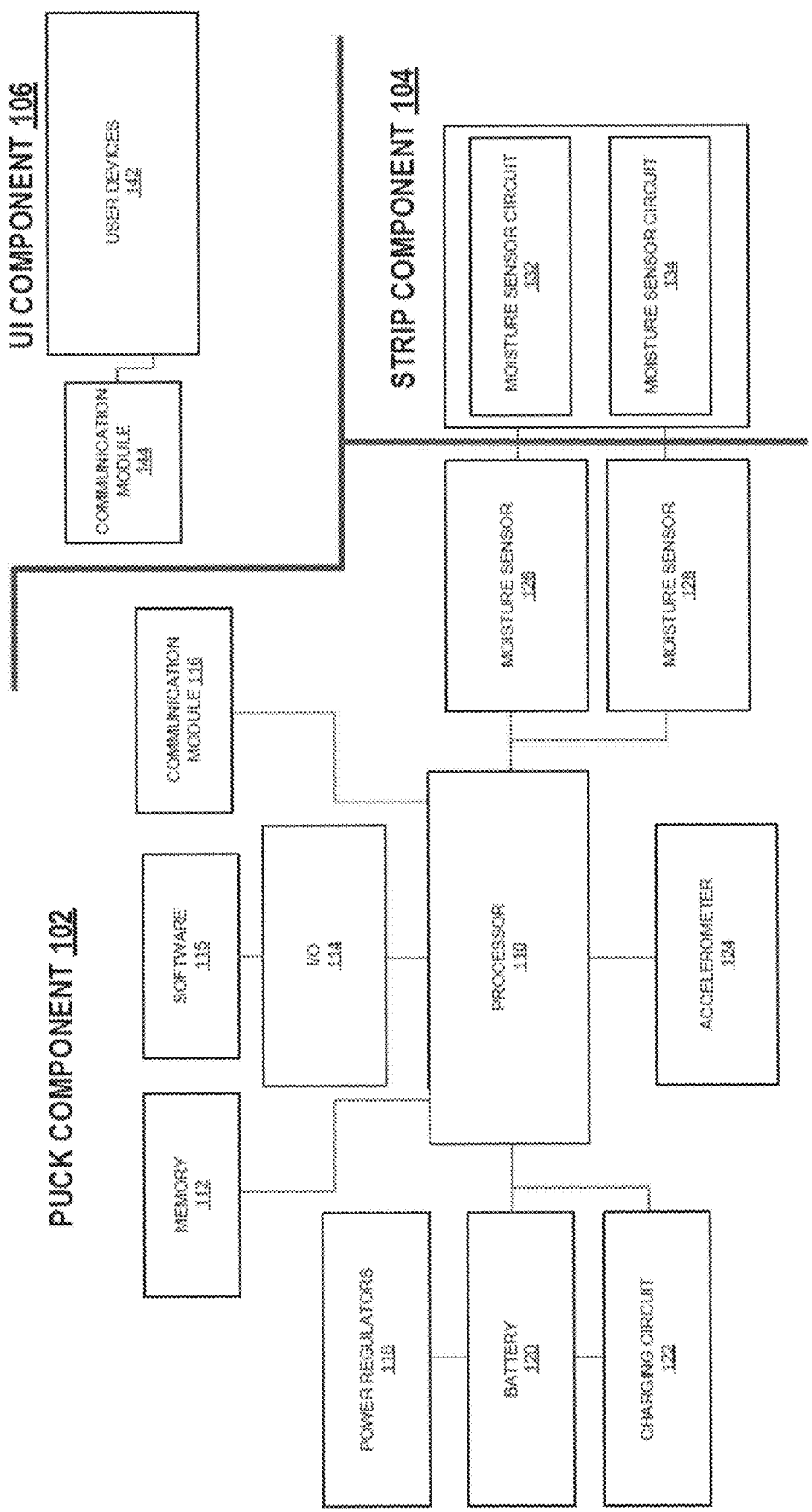
FIG. 1 illustrates an exemplary system for monitoring health condition of an individual via a wearable device, according to some embodiments.

Disclosed herein is a wearable device configured to be attached to an individual's clothing (e.g., diaper) for detecting certain events (e.g., urination, defecation, falling) of the individual, monitoring health condition of the individual over time, and providing automatic alerts and data analytics. In some embodiments, the wearable device comprises a puck component that can be repeatedly cleaned and reused, and a strip component that can be replaced as needed. The combination of the puck component and the strip component provides a lightweight and economic solution for providing accurate monitoring of the individual's health condition over time. Also disclosed herein are methods, systems, apparatuses, and non-transitory computer-readable storage media for enabling the wearable device and its functionalities.

By providing real-time and accurate monitoring of an individual's health, embodiments of the present invention can effectively prevent health degradation (e.g., due to skin rashes and infections, due to falls) of elderly individuals while reducing intrusive check-ups. Embodiments of the present invention can provide robust health profiling without requiring use of cumbersome equipment and significant manpower, thus reducing overall operational cost of care facilities. Embodiments of the present invention can further reduce or minimize incident-related expenses.

Accordingly, embodiments of the present invention can improve the lives of patients and medical staff and allow care facilities to streamline their operations and reduce costs and liabilities.

The following description sets forth exemplary methods, parameters, and the like. It should be recognized, however, that such description is not intended as a limitation on the scope of the present disclosure but is instead provided as a description of exemplary embodiments.

Although the following description uses terms "first," "second," etc. to describe various elements, these elements should not be limited by the terms. These terms are only used to distinguish one element from another. For example, a first graphical representation could be termed a second graphical representation, and, similarly, a second graphical representation could be termed a first graphical representation, without departing from the scope of the various described embodiments. The first graphical representation and the second graphical representation are both graphical representations, but they are not the same graphical representation.

The terminology used in the description of the various described embodiments herein is for the purpose of describing particular embodiments only and is not intended to be limiting. As used in the description of the various described embodiments and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

The term "if" is, optionally, construed to mean "when" or "upon" or "in response to determining" or "in response to detecting," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]," depending on the context.

FIG. 1 illustrates an exemplary system 100 for monitoring health condition of an individual via a wearable device, according to some embodiments. The system comprises a puck component 102, a strip component 104, and a user interface ("UI" component) 106.

The puck component 102 can comprise an embedded integrated circuit in some embodiments. With reference to FIG. 1, the puck component 102 comprises a microprocessor or a microcontroller 110 (e.g., a low-power microcontroller), a power source (e.g., power regulators 118, a battery 120, and/or a charging circuit 122), a memory 112, an I/O component 114, software 115, a communication module 116, an accelerometer 124, and a plurality of moisture sensors 126 and 128. In some embodiments, the puck component comprises additional sensor components for measuring biometric data (e.g., temperature). In some embodiments, the puck component comprises one or more light-dependent sensors.

In some embodiments, the power source of the puck component comprises power regulators 118, a battery 120, a charging circuit 122, or any combination thereof. The power regulators can comprise one or more low-dropout ("LDO") regulators. The battery can comprises a lithium polymer ("LiPo") battery or a coin cell battery. The charging circuit can be a USB charging circuit. In some embodiments, a charging dock can be provided to recharge the battery of the puck component. One of ordinary skill should recognize that other types and designs of power sources can be used for powering the puck component.

The I/O component 114 of the puck component comprises any suitable components that can provide input (e.g., momentary buttons, keypad, touch screen) and any suitable components that can provide output (e.g., touch screen, haptics device, speaker). In some embodiments, the input component comprises one or more momentary buttons that can be used to turn on, turn off, reset the puck component. In some embodiments, the input component allows the user to make the puck component visible on a network for pairing (e.g., Bluetooth paring). In some embodiments, the output component comprises one or more LEDs that can provide signals (e.g., detected events, battery levels) via colors, blinking, patterns, or a combination thereof. In some embodiments, the I/O component communicates with the processor 110 via GPIO.

The communication module 116 can include any suitable devices capable of transmitting and receiving signals over a network, such as a network interface chip or device. The puck component can be connected to another device in any suitable manner, such as via a physical bus or wirelessly. In some embodiments, the communication module 116 can provide connection via Wifi, LoRa, Bluetooth, Zigbee, cellular, RF, any other network, or any combination thereof. The puck component may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines. In some embodiments, a network gateway component is provided (e.g., a LoRA gateway). The gateway can be a standalone device or incorporated into the puck component.

The memory 112 can be any suitable device that provides storage, such as an electrical, magnetic or optical memory including a RAM, cache, hard drive, or removable storage disk. Software 115, which can be stored in storage 112 and executed by processor 110, can include, for example, the programming that embodies the functionality of the present disclosure (e.g., as embodied in the devices as described below). Software 115 can also be stored and/or transported within any non-transitory computer-readable storage medium for use by or in connection with an instruction execution system, apparatus, or device, such as those described herein, that can fetch instructions associated with the software from the instruction execution system, apparatus, or device and execute the instructions. In the context of this disclosure, a computer-readable storage medium can be any medium, such as storage 112, that can contain or store programming for use by or in connection with an instruction execution system, apparatus, or device. In some embodiments, a separate memory unit (e.g., an SD card) can be provided. The memory unit can store software features and updates of the wearable device. In some embodiments, the separate memory unit can interface with the charging dock to install the software features and updates.

The software 115 can also be propagated within any transport medium for use by or in connection with an instruction execution system, apparatus, or device, such as those described above, that can fetch instructions associated with the software from the instruction execution system, apparatus, or device and execute the instructions. In the context of this disclosure, a transport medium can be any medium that can communicate, propagate or transport programming for use by or in connection with an instruction execution system, apparatus, or device. The transport readable medium can include, but is not limited to, an electronic, magnetic, optical, electromagnetic or infrared wired or wireless propagation medium. Software 115 can be written in any suitable programming language, such as C, C++, Java or Python. In various embodiments, application software embodying the functionality of the present disclosure can be deployed in different configurations, such as in a client/server arrangement or through a Web browser as a Web-based application or Web service, for example.

The accelerometer 124 of the puck component comprises any suitable device that can measure acceleration. Measurements of the accelerometer can be used to obtain location, shock, and orientation of the puck component. In some embodiments, the accelerometer 124 is a 3-axis, 14-bit programmable component communicatively coupled to the processor via I2C. In some embodiments, the accelerometer is used to detect body positions on three-axis. The accelerometer detects the position on all three-axis and determines a patient's orientation. Jolts, impacts, quick moments, falls, and drops are detected using three-axis data. Logic algorithms are used based on original body positioning. Patient location with hysteresis is recoded by detecting and logging movements over greater distances. The accelerometer uses interrupts to wake up the system from a deep sleep on desired detected events. In some embodiments, other types of sensors can be used to measure the position of the puck component, such as a gyro sensor or a magnetometer. In some embodiments, the system includes one or more inertial measurement units ("IMU") with an accelerometer, a gyroscope, a magnetometer, a temperature sensor, a 9-axis sensor I²C, and/or SPI output.

The moisture sensors 126 and 128 of the puck component can be resistive/voltage/current moisture sensors, inductive sensors, capacitive sensors, optical sensors, or any combination thereof. In some embodiments, the moisture sensors 126 and 128 can operate with the moisture sensor circuits 132 and 134 of the strip component 104, respectively, as described in detail below.

The user interface component 106 comprises one or more user devices 142 communicatively coupled with the puck component 102 via a communicator module 144. Devices 142 can be any suitable type of microprocessor-based device, such as a personal computer, workstation, server or handheld computing device (portable electronic device) such as a phone or tablet. In some embodiments, devices 142 comprise software applications (e.g., desktop applications of mobile apps) for providing visualizations and alerts based on data transmitted by the puck component. Exemplary user interfaces of the software application is described below with reference to FIG. 2B. The analytics displayed on the user interfaces can be calculated by the processor 110, by the user devices 142, by the cloud, or a combination thereof.

Figure 2A:
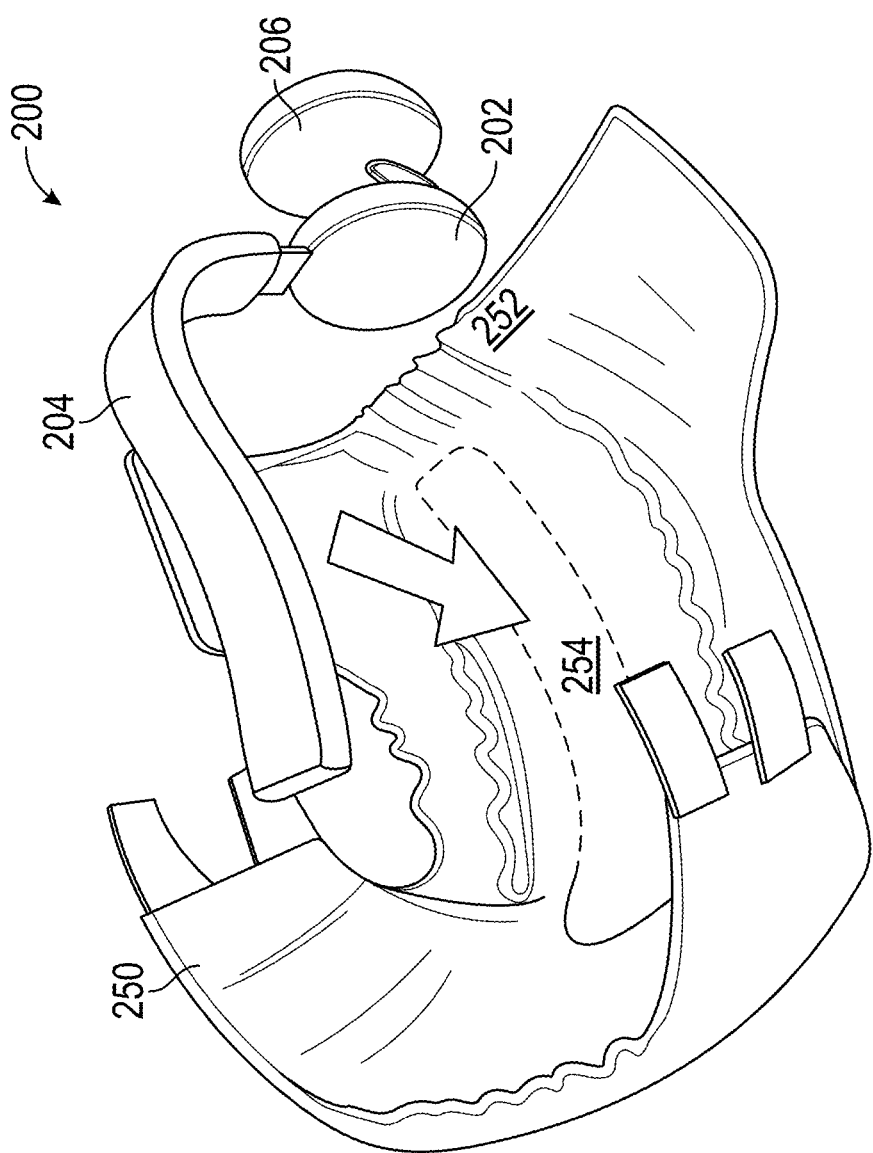
FIG. 2A illustrates an exemplary wearable device, according to some embodiments.

FIG. 2A illustrates an exemplary wearable device 200, according to some embodiments. The wearable device comprises a puck component 206 (e.g., the puck component 102 of FIG. 1). In the depicted example, the puck component 206 comprises a cradle 202 (e.g., cradle 508) for securing the along the brim 252 of the diaper 250 when the wearable device 200 is in use.

The wearable device 200 further comprises a strip 204 (e.g., the strip 104 of FIG. 1). The proximal end of the strip is secure to the puck component and thus to the diaper 250 when the device is in use. The strip extends along portion 254 of the diaper. As described herein, the strip 204 comprises circuits for detecting events occurring within the diaper, such as urination and defecation. The circuits can be arranged such that multiple events can be detected at multiple locations within the diaper, as described below.

Figure 2B:
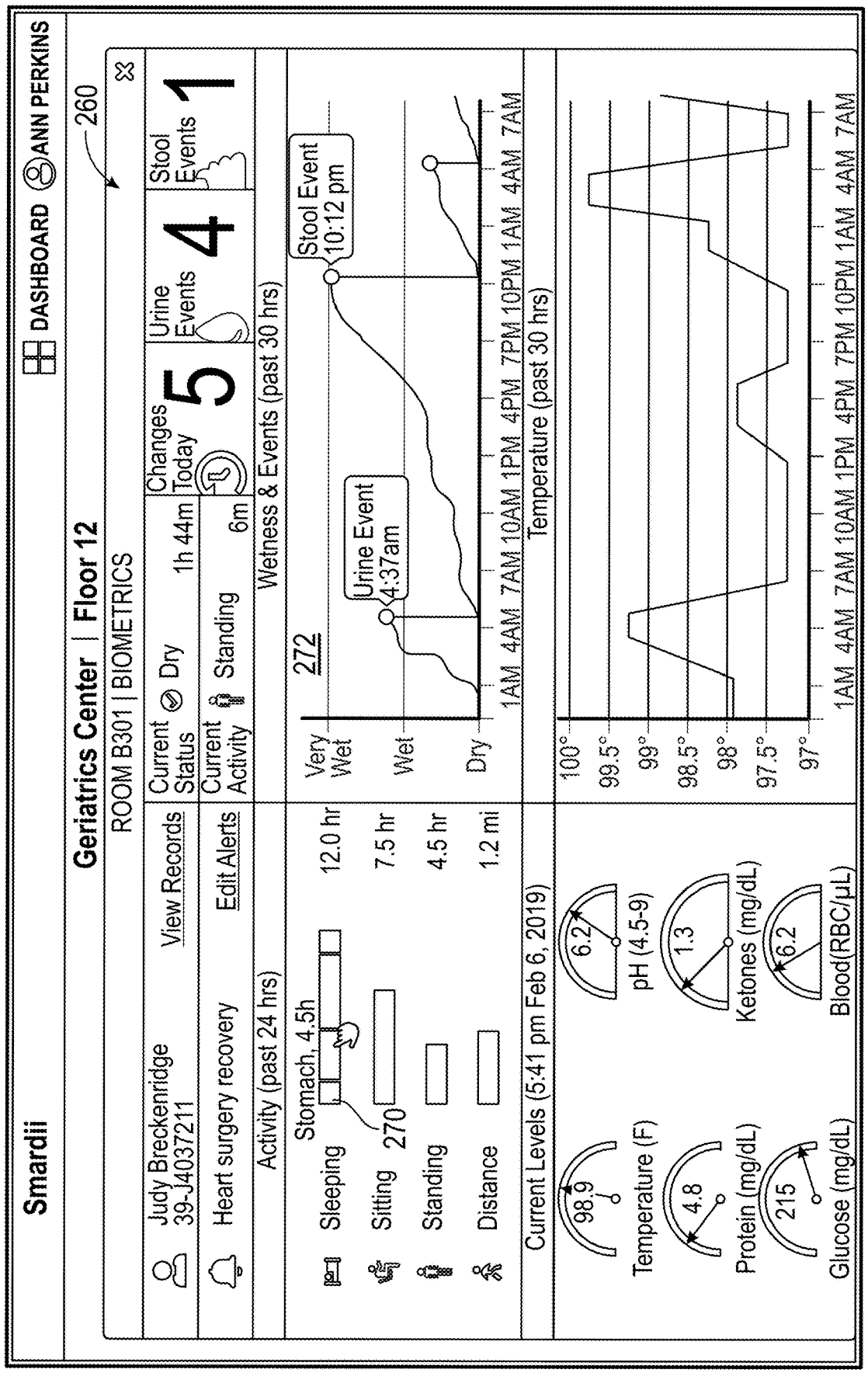
FIG. 2B illustrates an exemplary user interface of a software application, according to some embodiments.

FIG. 2B illustrates an exemplary user interface 260 of a software application, according to some embodiments. In some embodiments, the software application is cloud-based. In the depicted example, the user interface 260 displays a dashboard associated with an individual ("Judy Brekenridge"). The dashboard provides personal information of the individual (e.g., a unique identifier, a link to the individual's patient record).

Further, the dashboard provides a plurality of current/recent measurements of the individual, including a current status of the wearable device ("Dry" for 1 hour and 22 minutes), a current activity of the individual ("Standing" for 6 minutes), and a plurality of biometric measurements (e.g., temperature, pH, protein, ketones, glucose, and red blood cell concentration). The measurements are based on the data obtained and transmitted by the puck.

Further, the dashboard provides a summary of events, such as the number of diaper changes ("5"), the number of urine events ("4"), the number of stool events ("1") within a given time period. In addition, the dashboard further provides a summary of the individual's activities within a given time period. As shown by UI 270, the dashboard can provide a breakdown of the individual's sleeping time by body positioning. The dashboard further provides, as well as graphic representations 272 of the individual's measurements over time.

Figure 2C:
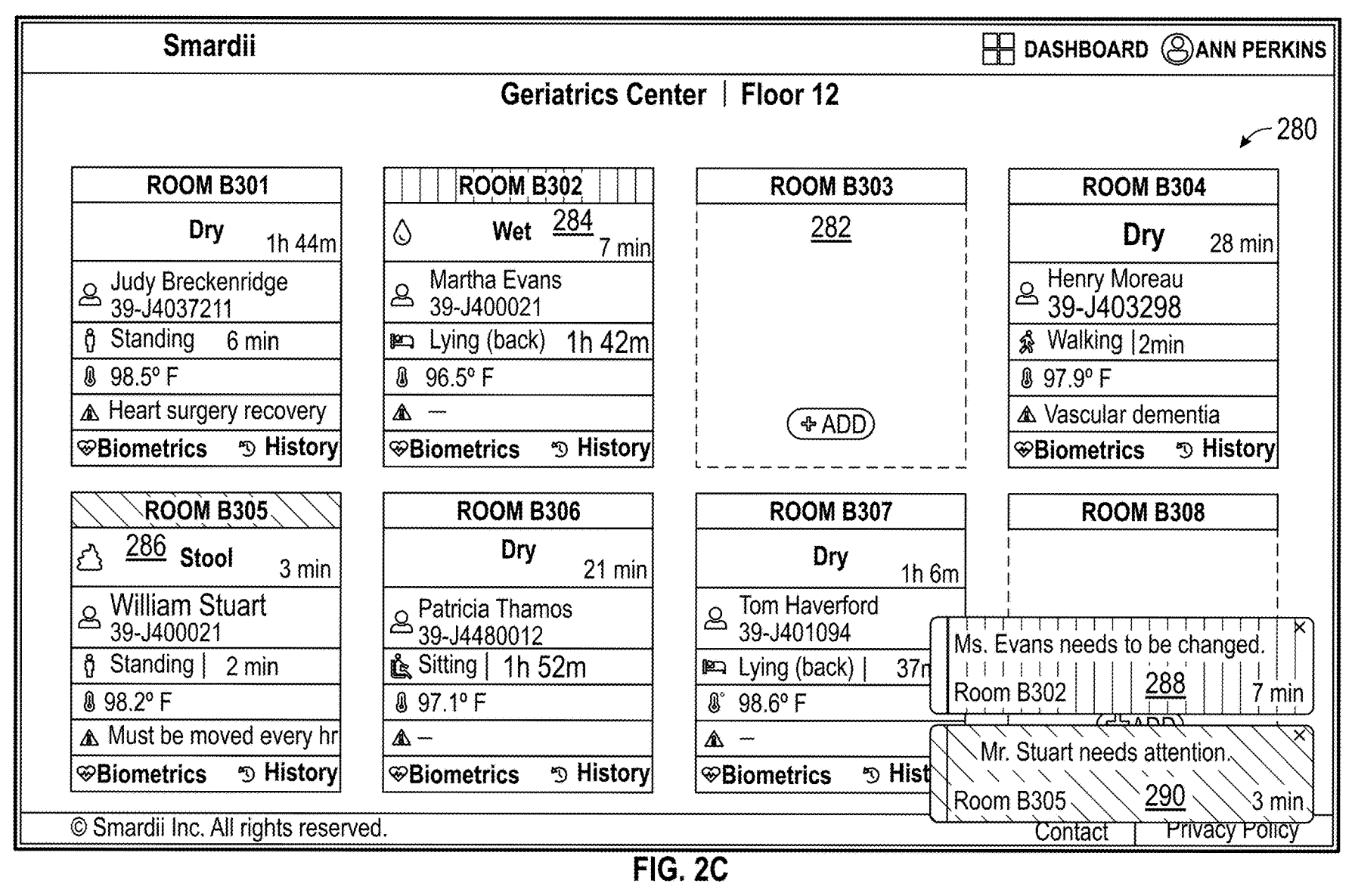

FIG. 2C illustrates another exemplary user interface 280 of the software application, according to some embodiments. The user interface 280 provides a "room" view tailored to a medical staff member ("Ann Perkins"). The room view includes a plurality of tiles corresponding to a plurality of rooms that the medical staff is responsible for in the care facility. Each tile shows a current status of the wearable device worn by the respective patient (e.g., "Dry," "Wet"), a current activity of the patient (e.g., "Standing for 6 minutes," "Walking for 2 minutes"), and other biometrics (e.g., temperature). Upon selection of each tile, a patient-specific page (e.g., user interface 260) can be shown. When a room is vacant, the respective tile 282 is shown as empty. When a patient is newly admitted, an authorized user can click on "ADD" to link the room to the patient (e.g., linking the room to an existing record of the patient in the database).

As shown by tiles 284 and 286, the color of the tiles can update to signify that an event has occurred (e.g., urination, stool) and that an action needs to be taken. Further, alerts 288 and 290 can be displayed such that the medical staff can be notified even when the user interface 280 is not in focus.

FIG. 2D illustrates another exemplary user interface 292 of the software application, according to some embodiments. As shown by tile 294, the respective patient "Martha Kensington" is associated with a setting "Must be moved every hour." As such, the tile automatically changes color when the patient needs to be moved. An alert 296 is also displayed. A plurality of settings can be associated with each patient, and the software application can automatically send alerts accordingly.

FIG. 3A illustrates an exemplary exploded view of a flexible circuit component 300 of a strip component, according to some embodiments. The flexible circuit component 300 is configured to be sandwiched between two elongated sheets to form a strip component of a wearable device in some embodiments. The flexible circuit component comprises three layers: a base layer 302, a conductor layer 304, and a dielectric layer 306. The conductor layer of the flexible circuit component comprises conductive pads, and some of the conductive pads are configured to interface with two moisture sensors within a puck component, as described below with reference to FIG. 3B.

FIG. 3B illustrates exemplary top view (skin-facing) of the flexible circuit component with the conductive layer exposed, according to some embodiments. At the left (or proximal) end of the flexible circuit component, the conductor layer comprises two pairs of conductive pads. The first pair of conductive pads 312 and 314 are configured to interface with a first moisture sensor within the puck (e.g., a urine sensor). Specifically, when a proximal end portion of the flexible circuit component is enclosed in the puck component, the first pair of conductive pads 312 and 314 is in contact with circuitries of the first sensor within the puck via the openings 320 (FIG. 3A) on the dielectric layer. The first pair of conductive pads are connected to conductive tracks 320 and 322, which extend along approximately half of the flexible circuit component. At the end of the conductive tracks 320 and 322 are distal conductive pads 352 and 354. As shown in FIG. 3A, the dielectric layer has slots 336 (FIG. 3A) to expose the distal conductive pads to moisture in the specific locations, while covering the conductive tracks.

In operation, the puck component measures the resistance between the distal conductive pads 352 and 354 to detect presence of moisture (e.g., urine). The circuit is open when the diaper is dry but closed when urine flows through the slots 336 and bridges the gap between the distal conductive pads.

Similarly, the second pair of conductive pad 316 and 318 are configured to interface with a second moisture sensor within the puck (e.g., a stool sensor). Specifically, when the proximal end portion of the flexible circuit component is enclosed in the puck component, the second pair of conductive pads are in contact with circuitries of the stool sensor within the puck via the openings 320 on the dielectric layer. The second pair of conductive pads are connected to conductive tracks 324 and 326, which extend along approximately the entirety of the flexible circuit component. At the end of the conductive tracks 324 and 326 are distal conductive pads 356 and 358. As shown in FIG. 3A, the dielectric layer has opening 334 to expose the distal conductive pads to moisture in the specific locations, while covering the conductive tracks.

In operation, the puck component measures the resistance between the distal conductive pads 356 and 358 to detect presence of moisture (e.g., stool). The circuit is open when the diaper is dry but closed when stool flows through the opening 334 and bridges the gap between the distal conductive pads.

In FIG. 3A, a plurality of holes 335 are provided on the dielectric layer 306 and the base layer 302 such that fluid (e.g., urine) can flow through the strip. In the depicted embodiment, all conductive pads are exposed via the dielectric layer and no conductive pads are exposed via the base layer. In some embodiments, conductive pads are exposed via the base layer to avoid sensing perspiration.

In some embodiments, the flexible circuit component 300 comprises one or more traditional flexible printed circuits ("FPC"). FPCs are made with photolithographic technology or chemically etched. They can have a polyimide, PEEK, or polyester substrate base layer. The conductors (e.g., conductive pads) can be metal foil (i.e., copper) bonded to the base layer. Dielectric layer (e.g., PET) bonded on top of conductor layer acts as electrical insulator. In some embodiments, FR4 material can be added as a stiffener if needed in certain areas. Connectors and certain components can be installed on the circuit. A FPC bonds the layers together with adhesive.

Figure 3C:
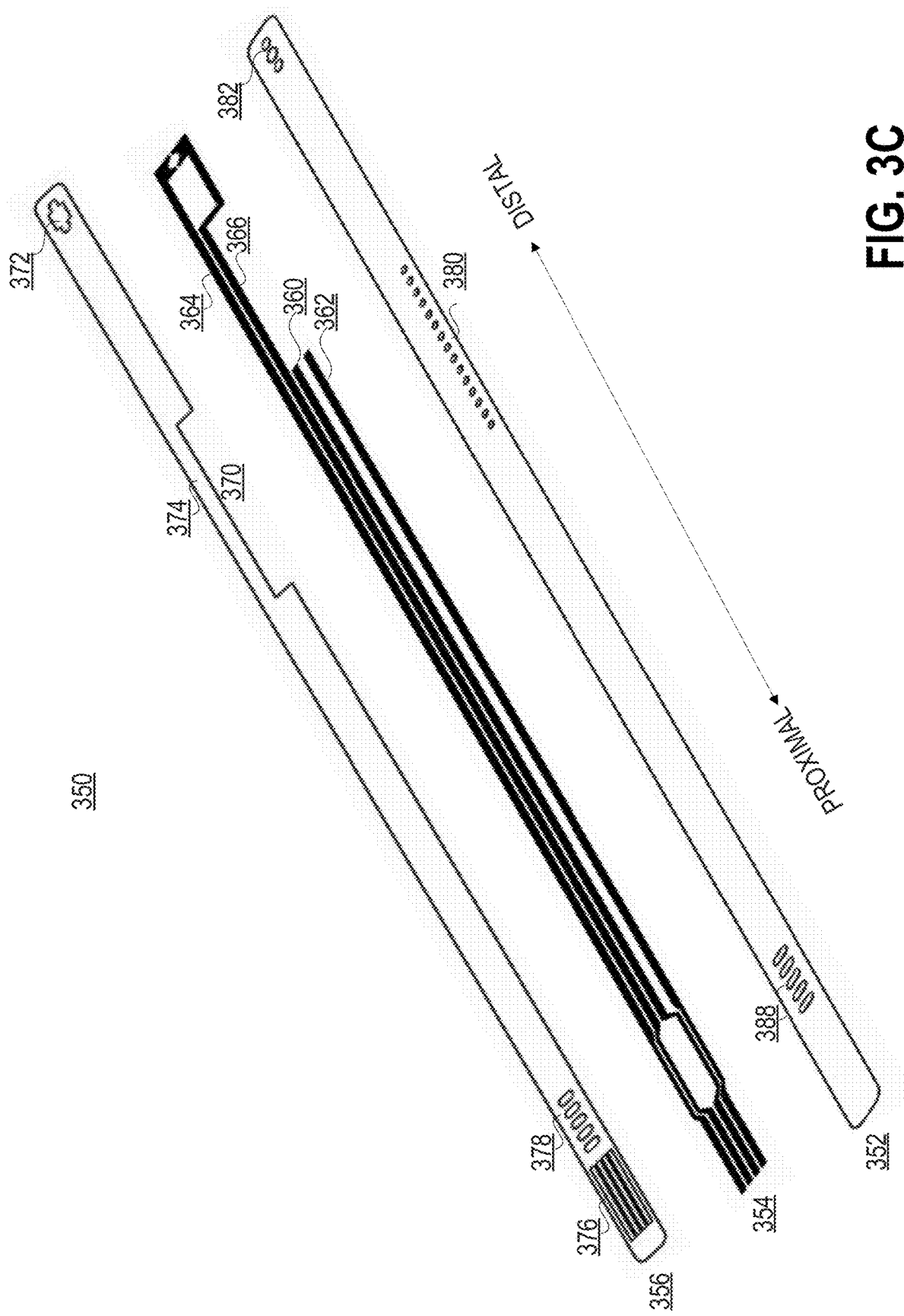
FIG. 3C illustrates an exemplary view of another flexible circuit component, according to some embodiments.
Figure 3D:
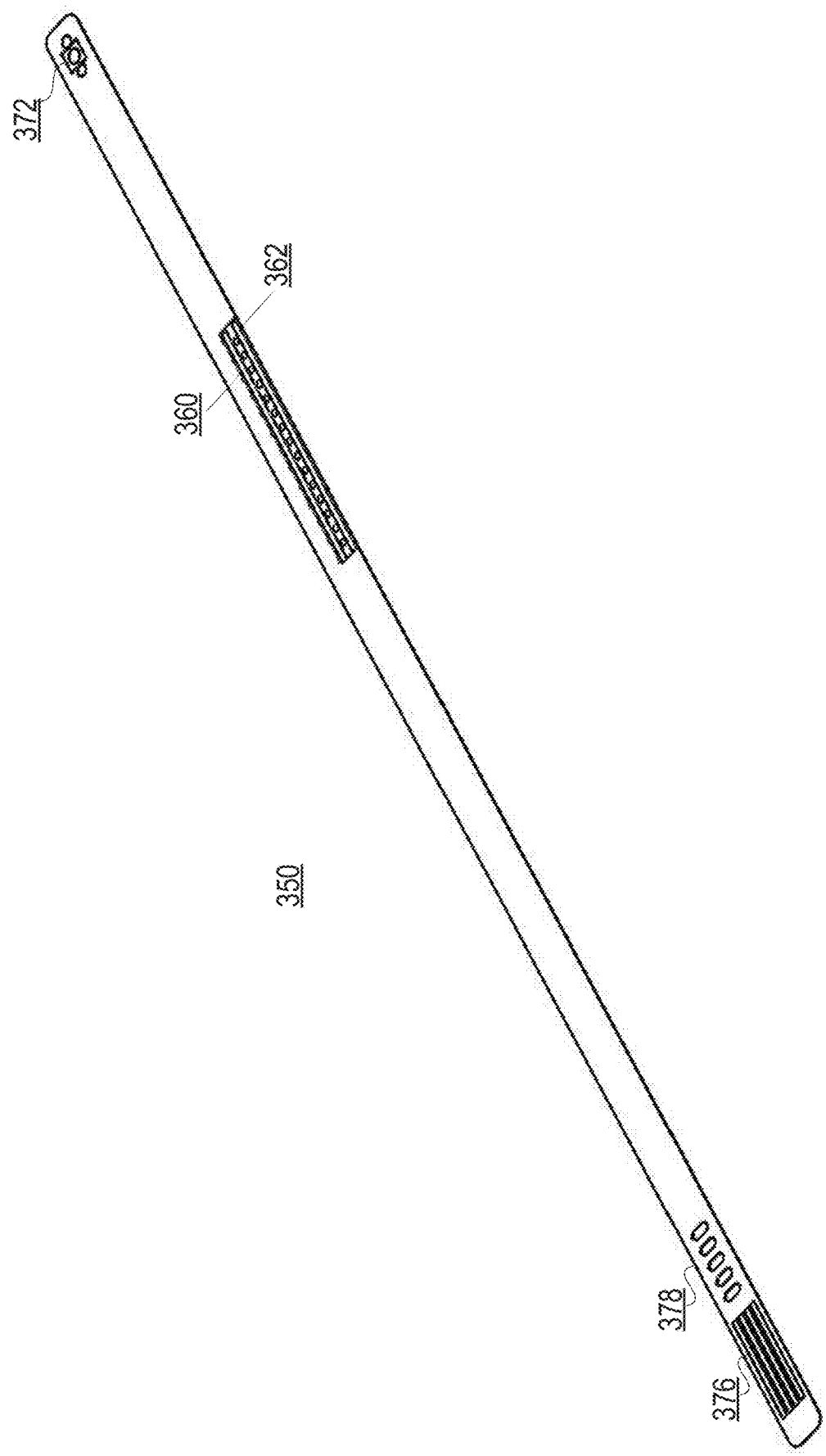
FIG. 3D illustrates an exemplary view of the flexible circuit component, according to some embodiments.

In some embodiments, the flexible circuit component 300 comprises one or more conductive ink flexible printed circuits. They can be made by applying conductive ink to substrate through screen printing, flexographic printing, gravure, offset lithography, or inkjet. They can have a PET base layer. The conductors can be thixotropic liquid (then cured). A conductive ink flex circuit does not use adhesive to bond the layers together, but must be cured. In some embodiments, the circuit can be manufactured by screen printing conductive ink onto PET, or by flexographic printing. FIGS. 3C-3D illustrates an exemplary exploded view of another flexible circuit component 350 of a strip component, according to some embodiments. FIG. 3C illustrates an exemplary exploded view of the flexible circuit component 350. The flexible circuit component 350 comprises three layers: a base layer 352, a conductive layer 354, and an insulating layer 356.

Similar to the conductive layer 304 of FIG. 3A, the conductive layer 354 comprises two circuits: one interfacing with a first moisture sensor in the puck to detect a first event (e.g., urination) and one interfacing with a second moisture sensor in the puck to detect a second event (e.g., defecation). The first circuit is formed by conductive lines 360 and 362, where the proximal ends of the lines 360 and 362 are configured to interface with the first moisture sensor in the puck (e.g., a urine sensor). The second circuit is formed by lines 364 and 366, where the proximal ends of the lines 364 and 366 are configured to interface with the second moisture sensor in the puck (e.g., a stool sensor).

Above the conductive layer 354 is the insulating (or dielectric) layer 356. The insulating layer can be made of waterproof material to protect the conductive layer and selectively expose specific portions of the conductive layer. Specifically, the insulating layer has a recess 370 to expose the distal portions of the lines 360 and 362. Accordingly, when the wearer urinates, the moisture can come into contact with the exposed portions of 360 and 362 and close the first circuit, thus triggering detection of the urination by the first sensor in the puck.

The insulating layer also has an opening 372 to expose the distal portions of lines 364 and 366. Accordingly, when the wearer defecates, the moisture can come into contact with the exposed portions of lines 364 and 366 and close the second circuit, thus triggering detection of the stool by the second sensor in the puck. The insulating layer protects the rest of lines 364 and 366 such that only moisture occurring at the opening 372 would close the second circuit. For example, if the moisture occurs around the distal ends of lines 360 and 362 (e.g., due to urination), it would not affect the second circuit because lines 364 and 366 are protected by portion 374 of the insulating layer.

The insulating layer also comprise four slots 376 to expose the proximal portions of lines 360, 362, 364, and 366. Accordingly, when the flexible circuit component 350 is coupled to the puck, the four lines are in contact with the corresponding sensor circuitries in the puck via the slots. The insulating layers also comprise a plurality of positioning holes 378, which can help to securely couple the strip to the puck, as described herein.

In operation, the puck component measures the resistance between the lines 360 and 362 to detect presence of moisture (e.g., urine). The first circuit is open when the diaper is dry but closed when urine flows through the recess 370 and bridges the gap between the distal portions of the lines 360 and 362. Similarly, the puck component also measures the resistance between the lines 364 and 366 to detect presence of moisture (e.g., stool). The second circuit is open when the diaper is dry but closed when stool flows through the opening 372 and bridges the gap between the distal portions of the lines 364 and 366.

The base layer 352 comprises holes 380 and 382 to allow excretion (e.g., urine, stool) to flow through the flexible circuit component. The base layer further comprises holes 388 that line up with holes 378, which can help to securely couple the flexible circuit to the puck, as described herein.

FIG. 3D illustrates a perspective view of the flexible circuit component 350, in accordance with some embodiments. As shown, much of the conductive layer is protected by the top insulating layer other than a proximal section, a middle section, and a distal section. Specifically, the four lines of the conductive layer at the proximal section are exposed by slots 376 so that they can interface with the circuitries in the puck. When the wearer urinates, moisture can come into contact with lines 360 and 362 in the middle section of the flexible circuit component, and then flow through the holes 380 of the base layer. When the wearer defecates, moisture can come into contact with lines 364 and 366 (not depicted in FIG. 3D) via the distal opening 372 and flow through the holes 382 of the base layer.

In some embodiments, the flexible circuit component 350 comprises one or more traditional flexible printed circuits ("FPC"). FPCs are made with photolithographic technology or chemically etched. They can have a polyimide, PEEK, or polyester substrate base layer. The conductors (e.g., conductive pads) can be metal foil (i.e., copper, silver) bonded to the base layer. Insulating layer (e.g., PET) bonded on top of conductor layer acts as electrical insulator. In some embodiments, FR4 material can be added as a stiffener if needed in certain areas. Connectors and certain components can be installed on the circuit. A FPC bonds the layers together with adhesive.

In some embodiments, the flexible circuit component 350 comprises one or more conductive ink flexible printed circuits. They can be made by applying conductive ink to substrate through screen printing, flexographic printing, gravure, offset lithography, or inkjet. They can have a PET base layer. The conductors can be thixotropic liquid (then cured). A conductive ink flex circuit does not use adhesive to bond the layers together, but must be cured. In some embodiments, the circuit can be manufactured by screen printing conductive ink onto PET, or by flexographic printing.

In FIGS. 3C and 3D, the exposed proximal portions of the conductive lines 360-366 serve as conductive pads that interface with the puck. While the conductive pads described herein can be of a circular shape (e.g., FIGS. 3A-B) or an elongated shape (e.g., FIGS. 3C-D), it should be appreciated that conductive pads can be of any shape.

Figure 4A:
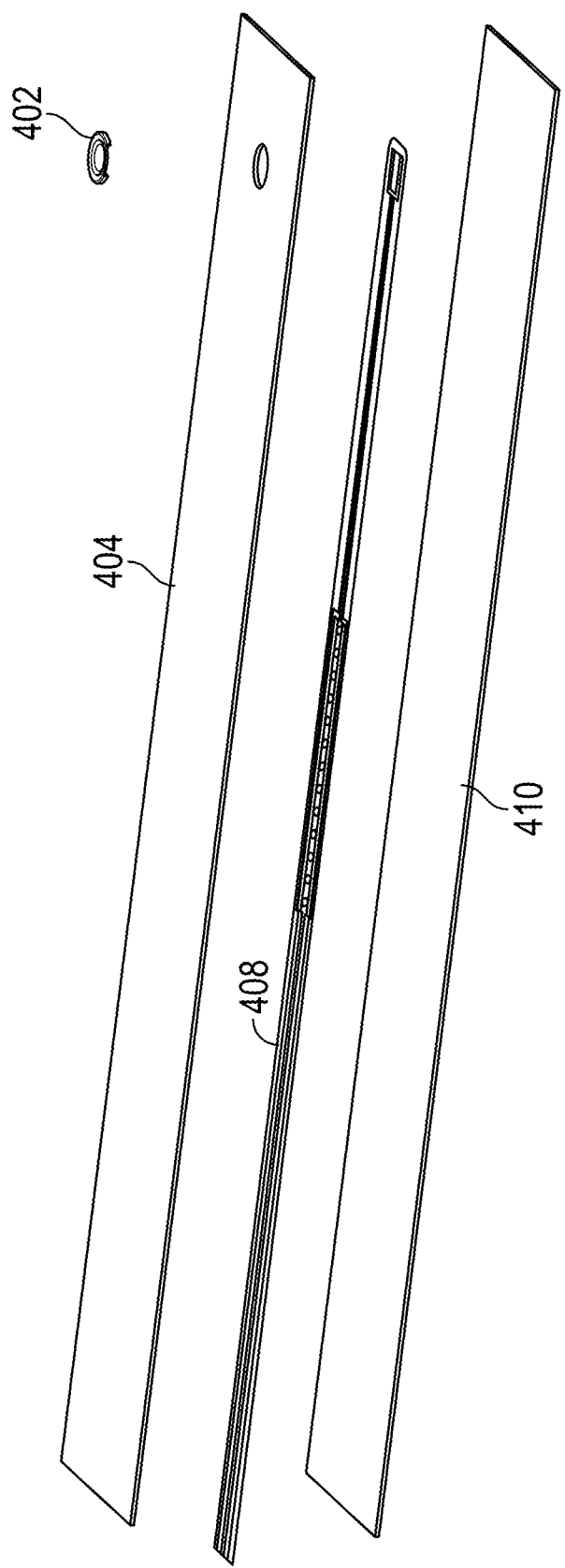
FIG. 4A illustrates an exemplary perspective view of a strip component, according to some embodiments.
Figure 4B:
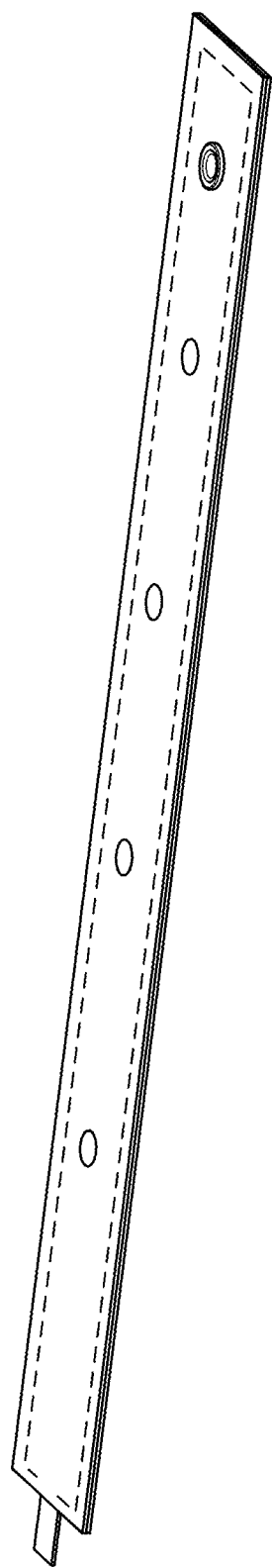
FIG. 4B illustrates an exemplary perspective view of a strip component, according to some embodiments.

FIG. 4A illustrates an exemplary perspective view of a strip component, according to some embodiments. As shown, the strip component comprises a spacer 402, a top sheet 404, a bottom sheet 406, and a flexible circuit component 408 (e.g., flexible circuit component 300 of FIG. 3A). In some embodiments, the top sheet and the bottom sheet are made of diaper material to provide for a comfortable contact. As shown in FIG. 4B, adhesives can be applied around the perimeter and along the center of the top or bottom sheets to glue the strip to the diaper. The proximal end of the flexible circuit component is exposed to interface (e.g., clip into) a puck component. Optionally, the bottom sheet 410 has peel-off adhesive on its back.

Figure 4C:
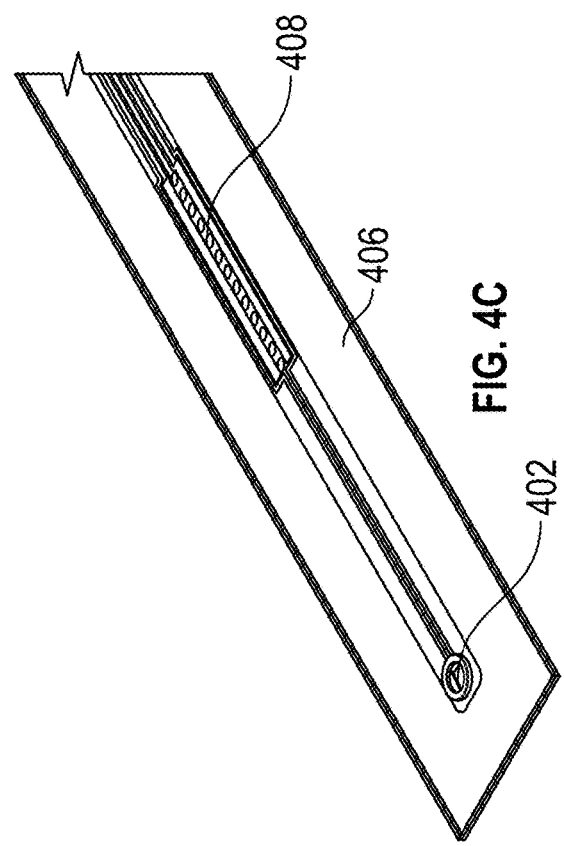
FIG. 4C illustrates an exemplary perspective view of a strip component, according to some embodiments.

FIG. 4C illustrates an exemplary perspective view of a distal end of a strip component, according to some embodiments. In FIG. 4C, the top sheet is not depicted, and only the spacer 402, the flexible circuit component 408, and the bottom sheet 406 are shown. The spacer 402 provides an opening to expose the distal conductive pads 450 (e.g., distal conductive pads 352 and 354), as shown in the detailed view of FIG. 4D.

Figure 4E:
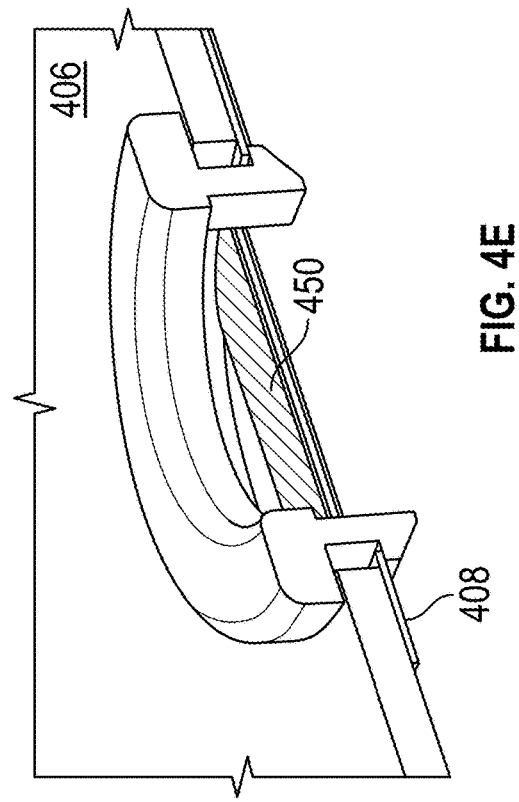
FIG. 4E illustrates an exemplary spacer, according to some embodiments.
Figure 4D:
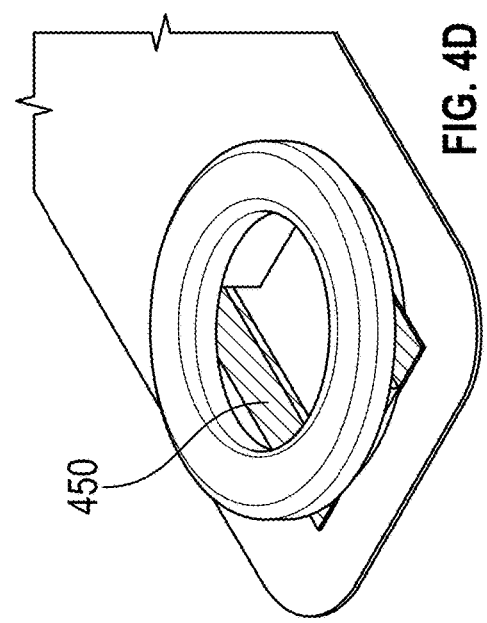
FIG. 4D illustrates an exemplary spacer, according to some embodiments.

FIG. 4E depicts an exemplary review of an spacer, according to some embodiments. In FIG. 4E, the bottom sheet is not depicted, and only the spacer 402, the flexible circuit component 408, and the top sheet 406 are shown. The top sheet 406 and the flexible circuit component 408 are captured by the spacer 420. The spacer creates a gap between skin and the conductive pad 450 on the flexible circuit component 408. Accordingly, the spacer 420 prevents the skin from coming in contact with the conductive pad 450 and triggering a false stool detection.

Figure 4F:
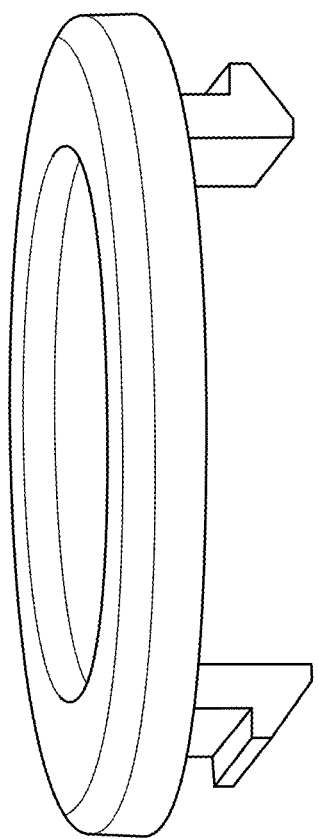
FIG. 4F illustrates exemplary spacers, according to some embodiments.
Figure 4F:
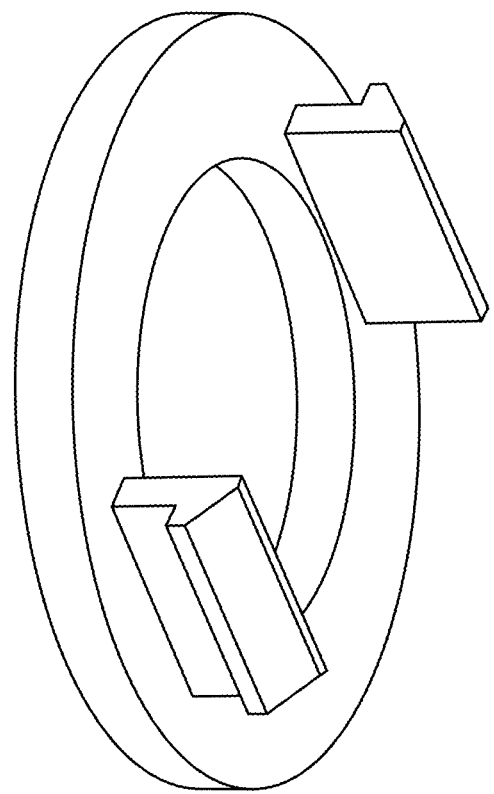

FIG. 4F illustrates additional perspective views of an exemplary spacer. In some embodiments, the spacer is injection molded. In some embodiments, the opening in the ring is between 4 mm to 5 mm in diameter, and the thickness is between 0.5 mm and 1.5 mm. In some embodiments, the spacer is optional and may be excluded from the strip component to achieve a lower profile and to reduce manufacturing cost.

While the embodiments in FIGS. 3A-4E include one circuit for detecting each type of event (e.g., one circuit for detecting urination and one circuit for detecting defecation), multiple circuits can be used to detect a single type of event. In some embodiments, the strip component can have multiple spacers. The spacers can be placed along the strip or enclose one another (e.g., in a Russian doll configuration). Each spacer encloses two conductive lines of a circuit and the circuit can be closed with a sufficient amount of moisture, thereby triggering the corresponding sensor. The system can determine that an event has occurred only if the number of triggered sensors exceeds a predefined threshold. Thus, the sensitivity of the detection can be adjusted to reduce false positives. In some embodiments, the number of triggered sensors can be used to determine the amount of urine, stool, etc.

Figures 5A, 5B:
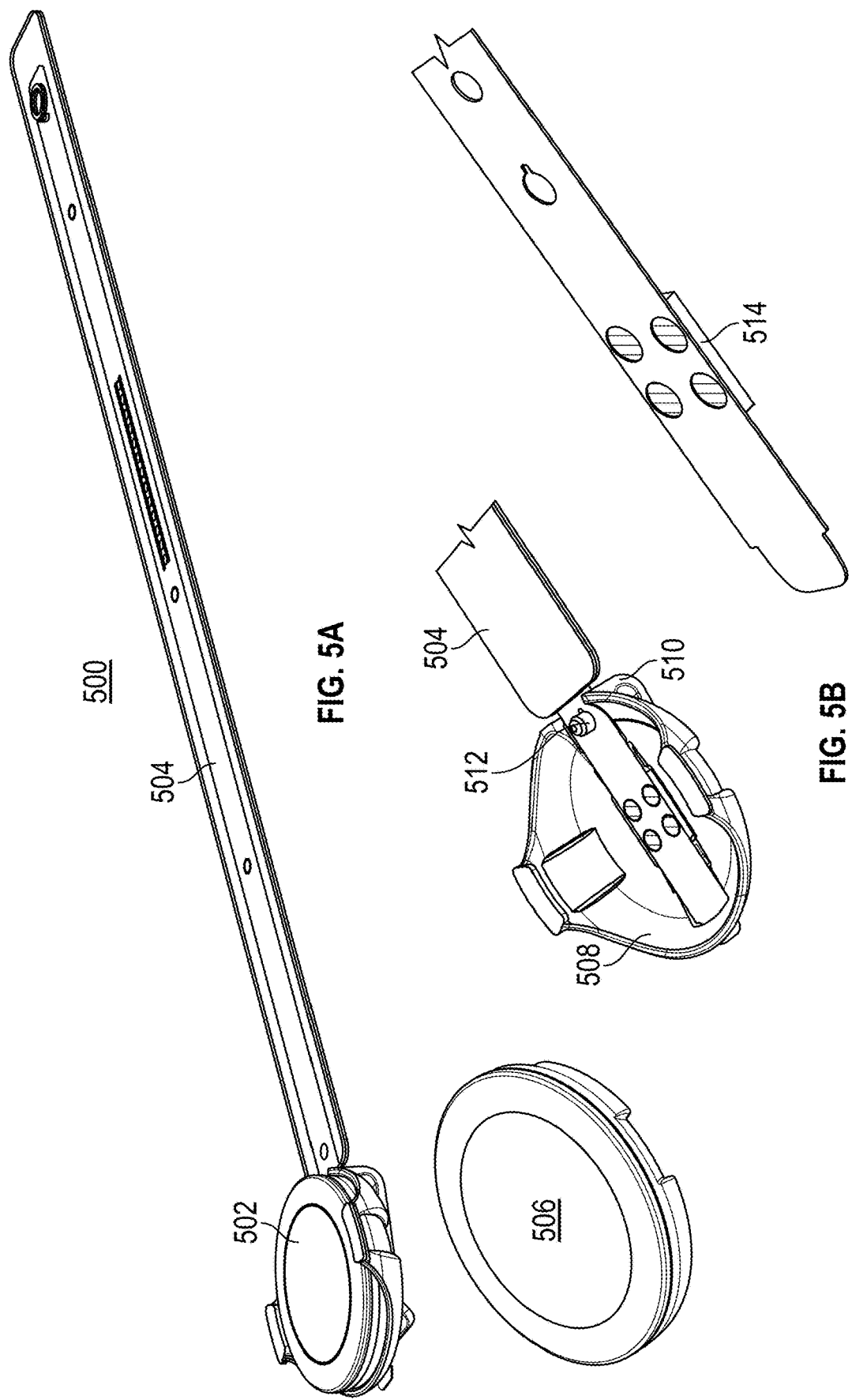
FIG. 5A illustrates an exemplary wearable device, according to some embodiments.
FIG. 5B illustrates exemplary components of a wearable device, according to some embodiments.

FIG. 5A illustrates an exemplary wearable device 500, according to some embodiments. The wearable device 500 comprises a puck component 502 and a strip 504. A proximal end portion of the strip 504 is enclosed within the puck component 502. In operation, the puck can be clipped onto an individual's clothing (e.g., diaper) and the strip is placed within the clothing to detect incidents within the clothing. In some embodiments, the strip can be embedded under the top sheet of the diaper (no contact with skin). In some embodiments, the stripe can be pealed and stuck onto the top layer (contact with skin).

FIG. 5B illustrates the coupling mechanism of the puck component and the strip component, according to some embodiments. The puck component 502 comprises a main housing 506 and a cradle 508. The main housing 506 can enclose a processor, a memory, software, communication module, I/O, sensors, accelerometer, and a power source as described above with reference to FIG. 1.

The cradle 508 comprises a knob 512 that allows the proximal end of the strip 504 to be attached to the cradle via a hole. The proximal end of the strip 504 comprises the proximal end of the flexible circuit component, which comprises four conductive pads (e.g. conductive pads 312, 314, 316, and 318) for interfacing with the sensors within the main housing 506. In some embodiments, a backing 514 is affixed on the other side of the flexible circuit component to ensure that the four conductive pads are securely in contact with the sensors within the main housing 506. The backing can be made of elastomer or foam.

The cradle 508 comprises a detachable buckle 510. The buckle is used to attach the puck component 500 to an individual's clothing. In some embodiments, the entire puck component 500 is fully ingress protected. The outer surface of the main housing and the cradle can be cleaned repeatedly, while the strip can be detached from the puck component and discarded as needed.

FIGS. 5C-D illustrate another exemplary wearable device, according to some embodiments. The wearable device comprises a cradle 552, a puck component 560, and a strip 570. During assembly (e.g., by a caregiver), a proximal portion of the strip is first affixed to the cradle 552. The cradle comprises a knob 554, and one of the positioning holes of the strip (e.g., one of holes 378) can be mounted on the knob 554 to fix the relative positioning between the strip and the cradle. As shown in FIGS. 5D and 5E, the puck can be then clipped onto the cradle via clamps of the cradle. The cradle also comprises an elevated tab 556 to push the strip against the puck and ensure that the four conductive lines (e.g., lines 360-366 in FIG. 3C) of the flexible circuit of the strip are securely in contact with the circuitries in the puck.

Figure 5I:
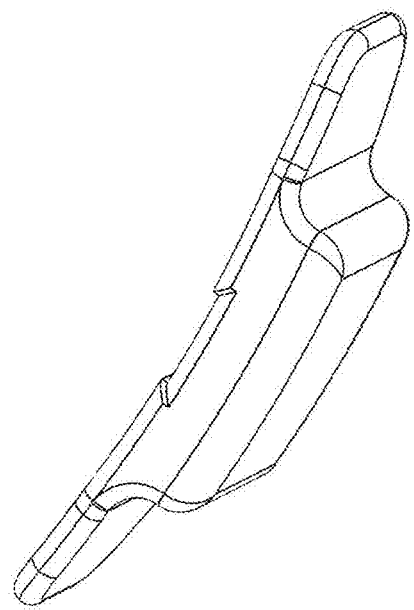
FIG. 5I illustrates an exemplary puck component, according to some embodiments.
Figure 5H:
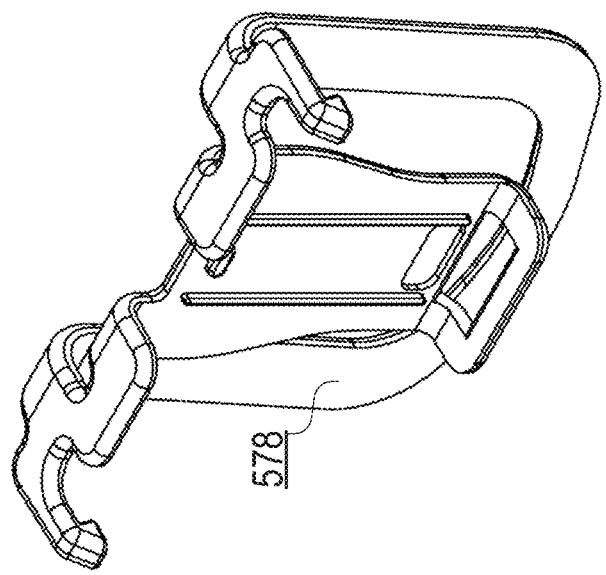
FIG. 5H illustrates an exemplary cradle, according to some embodiments.

FIGS. 5F and 5G illustrate an exemplary assembled wearable device, in accordance with some embodiments. FIG. 5F provides a top view of the device from the perspective of the wearer, while FIG. 5G provides a bottom view. The strip 570 can be placed in the diaper such that the spacer 574 is near the wearer's anus to detect stool. The puck can be placed outside the diaper, for example, by adhering the back 576 of the cradle to the outside of the diaper (e.g., via adhesives or Velcro) or by placing the puck within a pouch outside of the diaper. In some embodiments, the cradle can comprise a clip 578 as shown in FIG. 5H such that the cradle can be clipped over the rim of the diaper. The relative positioning between the puck and the spacer can be adjusted by amounting different positioning holes (e.g. 378) onto the knob of the cradle.

While the embodiments of the puck are shown to be rectangular (e.g., FIG. 5D) or circle (e.g., FIG. 2A), it should be appreciated that the puck can be of any shape. Further, as shown in FIG. 5I, the puck can have a reduced profile and curved to improve its wearability and comfort.

FIG. 6A depicts an exemplary process of monitoring a biological event associated with an individual, according to some embodiments. Process 600 is performed, for example, using one or more electronic devices implementing a software platform. In some examples, process 600 is performed using a client-server system, and the blocks of process 600 are divided up in any manner between the server and a client device. In other examples, the blocks of process 600 are divided up between the server and multiple client devices. Thus, while portions of process 600 are described herein as being performed by particular devices of a client-server system, it will be appreciated that process 600 is not so limited. In other examples, process 600 is performed using only a client device (e.g., user device 100) or only multiple client devices. In process 600, some blocks are, optionally, combined, the order of some blocks is, optionally, changed, and some blocks are, optionally, omitted. In some examples, additional steps may be performed in combination with the process 600. Accordingly, the operations as illustrated (and described in greater detail below) are exemplary by nature and, as such, should not be viewed as limiting.

At block 602, the system (e.g., one or more electronic devices) receives a first plurality of moisture measurements. At block 604, the system identifies a rise of moisture level within a first predefined threshold based on the plurality of moisture measurements. At block 606, the system receives a second plurality of moisture measurements taken after the first plurality of moisture measurements. At block 608, the system determines whether there is a drop of moisture level meeting a second predefined threshold (e.g., the rate of change exceeds a threshold) based on the second plurality of moisture measurements. At block 610, in accordance with a determination that there is the drop of moisture level, the system identifies a first event type. At block 612, in accordance with a determination that there is not the drop of moisture level meeting the predefined requirement, the system identifies a second event type.

The process 600 is based on the difference between fluid properties of urine and fecal: urine is largely water with similar capillary interaction with the diaper as water. On the other hand, fecal is generally less liquid. Diapers designed to quickly move liquid from the skin and wick it into the absorbance layer, but are less effective at absorbing fecal matters.

Figure 6B:
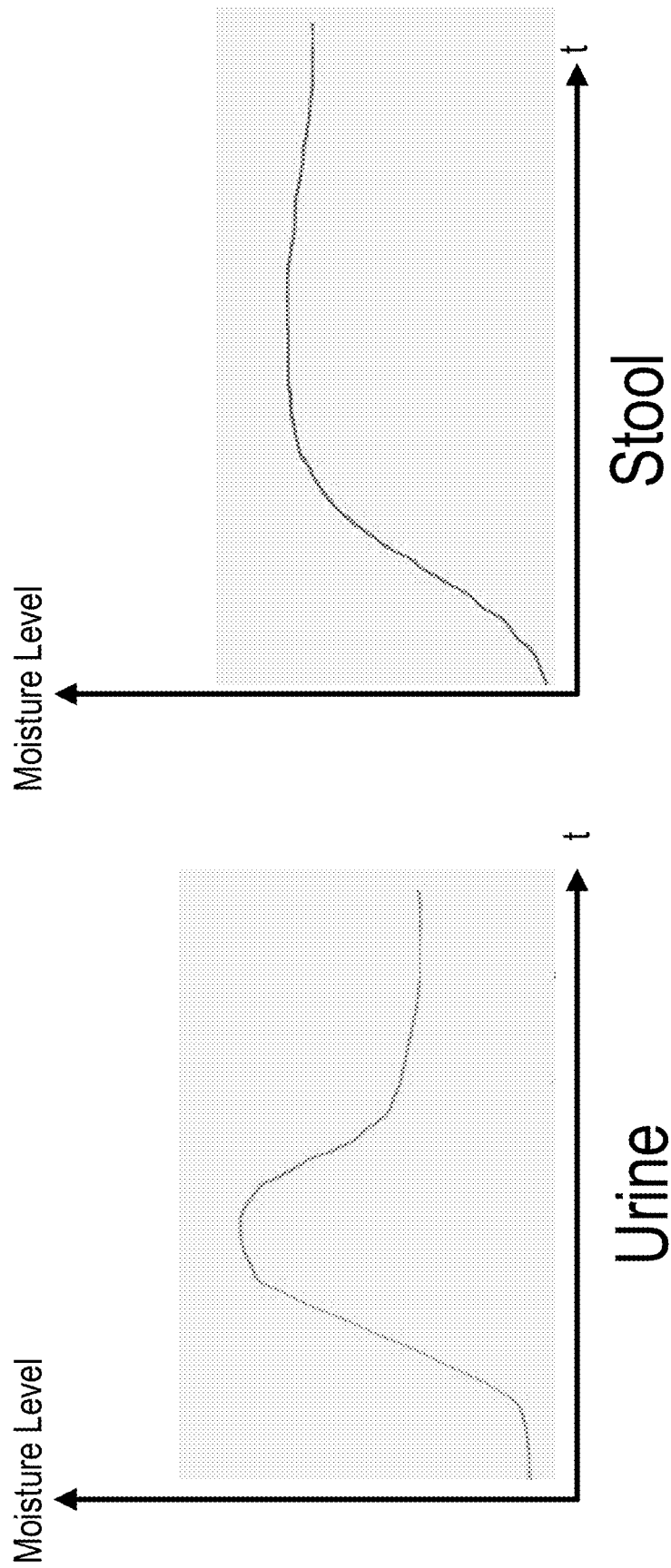
FIG. 6B illustrates exemplary trends of moisture level over time, according to some embodiments.

As shown in FIG. 6B, when urine floods the sensor, reading of moisture level peaks, then the wicking material and top-sheet start to perform as intended, pulling fluid away from the sensor and skin, down into the absorbent material of the diaper. Accordingly, there is a drop in moisture level if the "keep dry" property works as designed.

On the other hand, when fecal matter saturates the sensor, due to its property of being able to hold onto moisture better, it does not get wicked away very quickly. This prolongs the moisture sensor signal duration.

In some embodiments, the system can detect an event type (e.g., urination, defecation) based on moisture level. For example, the system can determine when a moisture level (e.g., based on resistance reading from the sensor) exceeds a predefined threshold. In accordance with a determination that the moisture level exceeds a predefined threshold, the system detects a first event type (e.g., urine, blood). In accordance with a determination that the moisture level does not exceed a predefined threshold, the system detects a second event type (e.g., stool).

In some embodiments, the system can detect an event type (e.g., urination, defecation) based on the locations of the sensors. For example, the system detects a first event type (e.g., urination, blood) if only the urine sensor (e.g., conductive pads 352 and 354) measures a moisture level above a threshold or both the urine sensor and the stool sensor (e.g., conductive pads 356 and 358) measure moisture levels above certain thresholds. This is because liquid such as urine would come into contact with the urine sensor (thus raising the moisture level) and possibly flow to reach the stool sensor. On the other hand, the system detects a second event type (e.g., stool) if only the stool sensor (e.g., conductive pads 356 and 358) measure moisture levels above a certain threshold. This is because solid such as stool would come into contact with the stool sensor but would generally not flow to reach the urine sensor.

In some embodiments, the system detects event types based on a combination (e.g., a weighted combination) of sensor location data, moisture level data, and rate of drop data.

In some embodiments, the duration of detected moisture (e.g., how long the moisture level stays above a certain threshold) can be used to determine how saturated the diaper is. For example, if the urine sensor detects moisture and it is determined that the moisture level stays above a certain threshold over a predefined period of time, it can be determined that the diaper is saturated. Accordingly, the system may issue a notification that the diaper needs to be changed. In some embodiments, the duration of moisture can be used to determine an amount of urine, stool, etc., accumulated in the diaper.

FIG. 7A illustrates operation of an exemplary fiber optical sensor and FIG. 7B illustrates the exemplary fiber optical sensor, according to some embodiments. As shown in FIG. 7B, a bundle of fibers (e.g., 3 fibers) 702 extends through a sensor pad (e.g., strip component) of a wearable device. The distal end of the fiber bundle is placed by a stool occlusion pocket 704. In some embodiments, the stool occlusion pocket at the same location as the gap created by the distal conductive pads (e.g., 356 and 358). Further, one or more return fibers 706 are placed by the stool occlusion pocket 704 across the gap. When the stool occlusion pocket is empty, light emitted by the fiber bundle 702 travels through the return fibers 706. When stool is introduced into the stool occlusion pocket, light emitted by the fiber bundle 702 is at least partially blocked by the stool.

The puck component comprises one or more light-dependent resistors. In some embodiments, the resistors are protocells, which are generally small, inexpensive, low-power, and durable. The resistors are connected to the fiber bundle and the return fibers to form a circuit. When stool is introduced into the stool occlusion pocket, the light received by the returned fibers decreases (and resistance increases). When the light decrease exceeds a predefined threshold, a stool event is detected.

Figure 7C:
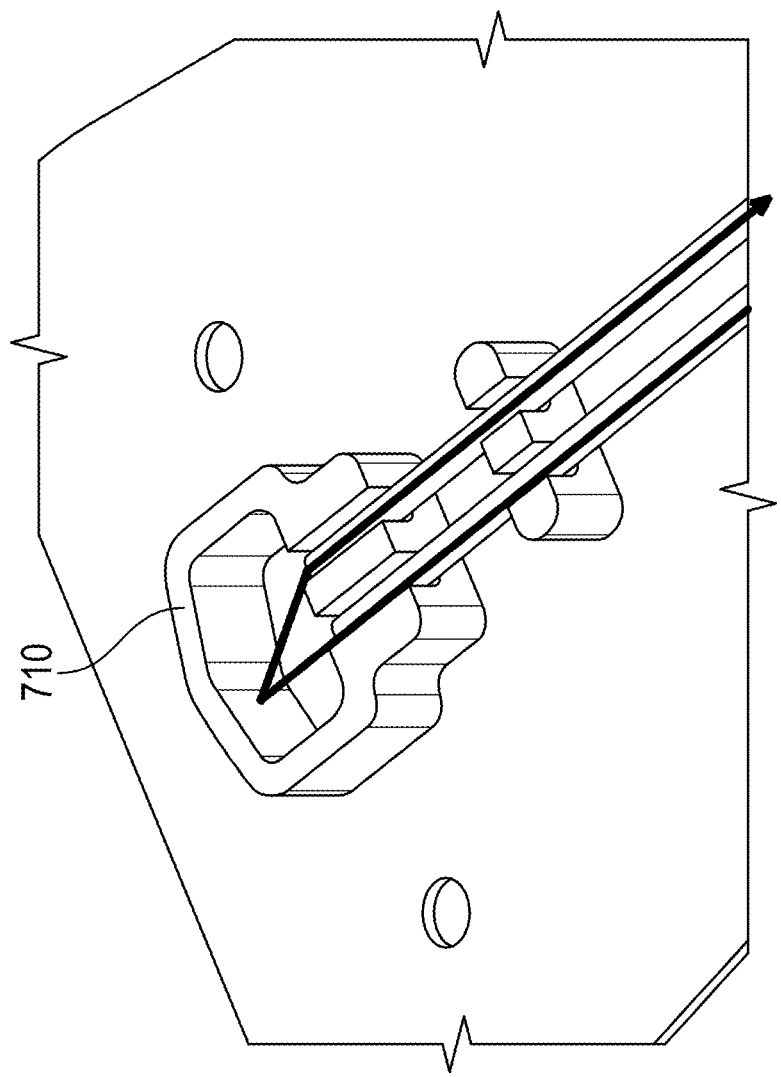
FIG. 7C illustrates operation of an exemplary fiber optical sensor, according to some embodiments.

FIG. 7C illustrates operation of another exemplary fiber optical sensor, according to some embodiments. When the stool occlusion pocket 710 is empty, light emitted by the fiber bundle travels through the return fibers, as shown by the path. When stool is introduced into the stool occlusion pocket, light emitted by the fiber bundle is at least partially blocked by the stool and only a portion of the emitted light reaches the return fibers. When the light decrease exceeds a predefined threshold, a stool event is detected.

Figure 8:
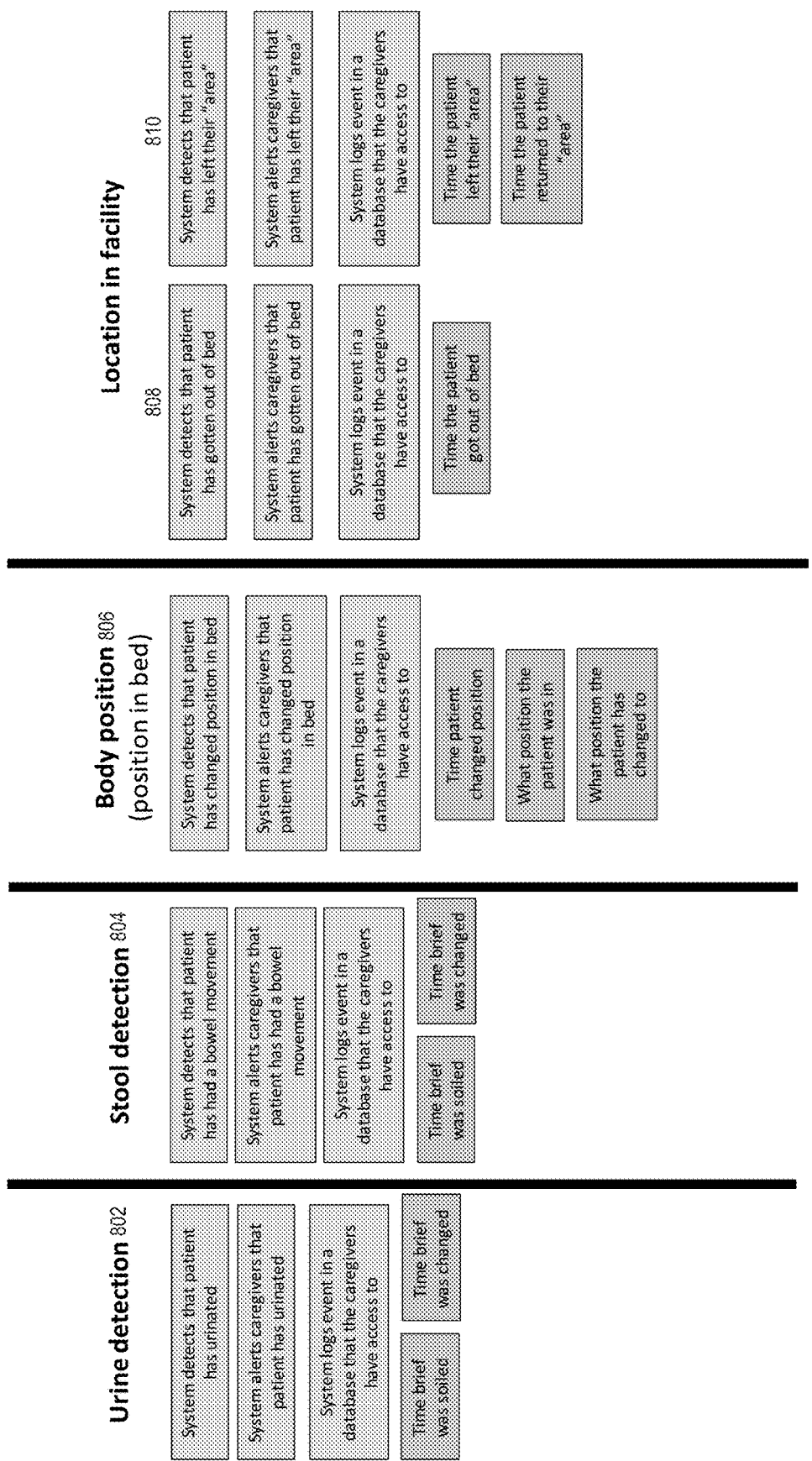
FIG. 8 illustrates exemplary processes of a wearable device, according to some embodiments.

FIG. 8 illustrates exemplary processes of a wearable device, according to some embodiments. In process 802, a system (e.g., one or more electronic devices) detects that patient has urinated, alerts caregivers of the event, and logs event in a database that caregivers have access to. In some embodiments, the system logs time of the event and time brief was changed (e.g., based on a reset input on the wearable device).

In process 804, a system (e.g., one or more electronic devices) detects that patient has had a bowel movement, alerts caregivers of the event, and logs event in a database that caregivers have access to. In some embodiments, the system logs time of the event and time brief was changed (e.g., based on a reset input on the wearable device).

In process 806, a system (e.g., one or more electronic devices) detects that patient has changed position in bed, alerts caregivers of the event, and logs event in a database that caregivers have access to. In some embodiments, the system logs time of the event, the position the patient was in, and the position the patient has changed to. The patient's body position (e.g., lying down, sitting up, standing, walking, on the back, on the left side, on the right side, on the stomach) can be automatically determined by the system based on the measurements of the accelerometer.

In process 808, a system (e.g., one or more electronic devices) detects that patient has gotten out of bed, alerts caregivers of the event, and logs event in a database that caregivers have access to. In some embodiments, the system logs time of the event. The patient's movement can be automatically determined by the system based on the measurements of the accelerometer.

In process 806, a system (e.g., one or more electronic devices) detects that patient has left a predefined area (e.g., a predefined room), alerts caregivers of the event, and logs event in a database that caregivers have access to. In some embodiments, the system logs time of the event and the time the patient returned to their area. The patient's movement can be automatically determined by the system based on the measurements of the accelerometer.

Figure 9:
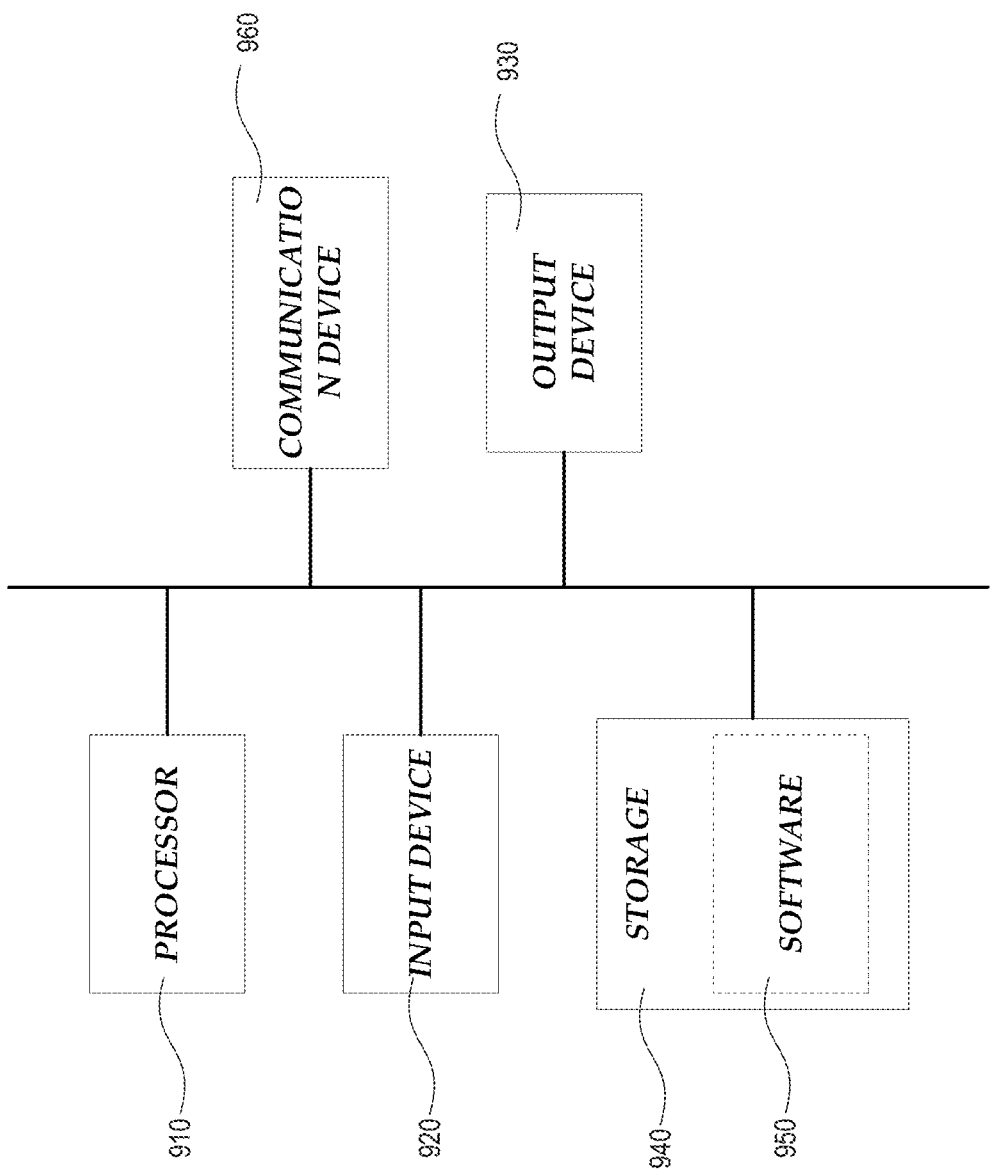
FIG. 9 illustrates an exemplary electronic device, according to some embodiments.

The operations described above with reference to FIG. 1-8 are optionally implemented by components depicted in FIG. 9.

FIG. 9 illustrates an example of a computing device in accordance with one embodiment. Device 900 can be a host computer connected to a network. Device 900 can be a client computer or a server. As shown in FIG. 9, device 900 can be any suitable type of microprocessor-based device, such as a personal computer, workstation, server or handheld computing device (portable electronic device) such as a phone or tablet. The device can include, for example, one or more of processor 910, input device 920, output device 930, storage 940, and communication device 960. Input device 920 and output device 930 can generally correspond to those described above, and can either be connectable or integrated with the computer.

Input device 920 can be any suitable device that provides input, such as a touch screen, keyboard or keypad, mouse, or voice-recognition device. Output device 930 can be any suitable device that provides output, such as a touch screen, haptics device, or speaker.

Storage 940 can be any suitable device that provides storage, such as an electrical, magnetic or optical memory including a RAM, cache, hard drive, or removable storage disk. Communication device 960 can include any suitable device capable of transmitting and receiving signals over a network, such as a network interface chip or device. The components of the computer can be connected in any suitable manner, such as via a physical bus or wirelessly.

Software 950, which can be stored in storage 940 and executed by processor 910, can include, for example, the programming that embodies the functionality of the present disclosure (e.g., as embodied in the devices as described above).

Software 950 can also be stored and/or transported within any non-transitory computer-readable storage medium for use by or in connection with an instruction execution system, apparatus, or device, such as those described above, that can fetch instructions associated with the software from the instruction execution system, apparatus, or device and execute the instructions. In the context of this disclosure, a computer-readable storage medium can be any medium, such as storage 940, that can contain or store programming for use by or in connection with an instruction execution system, apparatus, or device.

Software 950 can also be propagated within any transport medium for use by or in connection with an instruction execution system, apparatus, or device, such as those described above, that can fetch instructions associated with the software from the instruction execution system, apparatus, or device and execute the instructions. In the context of this disclosure, a transport medium can be any medium that can communicate, propagate or transport programming for use by or in connection with an instruction execution system, apparatus, or device. The transport readable medium can include, but is not limited to, an electronic, magnetic, optical, electromagnetic or infrared wired or wireless propagation medium.

Device 900 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

Device 900 can implement any operating system suitable for operating on the network. Software 950 can be written in any suitable programming language, such as C, C++, Java or Python. In various embodiments, application software embodying the functionality of the present disclosure can be deployed in different configurations, such as in a client/server arrangement or through a Web browser as a Web-based application or Web service, for example.

Exemplary methods, non-transitory computer-readable storage media, systems, and electronic devices are set out in the following items:

1. A method of monitoring a biological event associated with an individual, the method comprising:
   receiving a first plurality of moisture measurements;
   identifying a rise of moisture level within a first predefined threshold based on the plurality of moisture measurements;
   receiving a second plurality of moisture measurements taken after the first plurality of moisture measurements;
   determining whether there is a drop of moisture level meeting a second predefined threshold based on the second plurality of moisture measurements;
   in accordance with a determination that there is the drop of moisture level, identifying a first event type;
   in accordance with a determination that there is not the drop of moisture level meeting the predefined requirement, identifying a second event type.
2. The method of item 1, further comprising: automatically causing an alert based on an identified event type.
3. The method of any of items 1-2, wherein the first event type is excretion of bodily fluid.
4. The method of item 3, wherein the bodily fluid is urine or blood.
5. The method of any of items 1-4, wherein the second event type is excretion of stool.
6. The method of any of items 1-5, wherein determining whether there is a drop of moisture level meeting a second predefined threshold comprises: identifying the rise and the drop have occurred within a predefined time period.
7. The method of any of items 1-6, wherein determining whether there is a drop of moisture level meeting a second predefined threshold comprises: calculating a rate of drop of moisture level.
8. A wearable device for monitoring health condition of an individual, comprising:
   a puck component attachable to the individual's clothing, wherein the puck component comprises a circuit of a moisture sensor;
   a strip component configured to be placed within the individual's clothing,
     wherein a proximal end portion of the strip comprises a pair of conductive pads, and
     wherein the pair of conductive pads is configured to interface with the circuit of the moisture sensor while the proximal end portion of the strip is enclosed within the puck via a coupling mechanism.
9. The method of item 8, wherein the puck component comprises a main housing, and wherein the outer surface of the main housing exposes a pair of electrodes corresponding to the circuit of the moisture sensor.
10. The method of any of items 8-9, wherein the puck component comprises a cradle attachable to the main housing to enclose the proximal end portion of the strip.
11. The method of item 10, wherein the cradle comprises a buckle.
12. The method of any of items 8-11, wherein the strip component comprises a flexible circuit.
13. A wearable device for monitoring health condition of an individual, comprising:
   a strip component comprising:
     a first pair of proximal conductive pads located on a proximal end portion of the strip;
     a first pair of distal conductive pads connected to the first pair of proximal conductive pads via one or more conductive tracks, wherein the first pair of proximal conductive pads and the first pair of proximal conductive pads are configured to detect a first event type;
     a second pair of proximal conductive pads located on a proximal end portion of the strip;
     a second pair of distal conductive pads connected to the first pair of proximal conductive pads via one or more conductive tracks, wherein the second pair of proximal conductive pads and the second pair of proximal conductive pads are configured to detect a first event type.
14. The device of item 13, wherein the first event type is excretion of bodily fluid.
15. The device of any of items 13-14, wherein the second event type is excretion of stool.
16. A wearable device for monitoring health condition of an individual, comprising:
   a strip component comprising a pair of conductive pads, wherein a gap is formed between the pair of conductive pads;
   a top sheet placed over the strip component, wherein the top sheet comprises a hole for exposing the pair of conductive pads;
   a spacer comprising a ring portion and two supports,
     wherein the ring portion is placed over the top sheet and comprises a hole for exposing the pair of conductive pads, and
     wherein the supports hold the top sheet and the strip component to create spacing between the top of the ring portion and the pair of conductive pads.
17. The wearable device of item 16, wherein the pair of conductive pads are located at a distal portion of the strip.
18. The wearable device of any of items 16-17, wherein the strip comprises a flexible circuit.
19. An system monitoring health condition of an individual, comprising:
   a strip component configured to be placed within the individual's clothing, wherein the strip component comprises:
     a gap configured to receive bodily waste,
     a first fiber configured to emit light across the gap, and
     a second fiber configured to receive the light emitted across the gap;
   a puck component attachable to the individual's clothing, wherein the puck component comprises a light-dependent resistor sensor, wherein the resistor sensor is connected to the first fiber and the second fiber.
20. The system of item 19, wherein the resistor sensor comprises a photocell.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

What is claimed is:

1. A method of monitoring a biological event associated with an individual, the method comprising:
    at a wearable device comprising:
        a puck component comprising a first moisture sensor and a second moisture sensor, and
        a strip component comprising a first circuit corresponding to the first moisture sensor and a second circuit corresponding to the second moisture sensor;
        receiving, at one of the first moisture sensor and the second moisture sensor, a first plurality of moisture measurements;
        identifying a rise of moisture level within a first predefined threshold based on the plurality of moisture measurements;
        receiving, at the same one of the first sensor and the second sensor, a second plurality of moisture measurements taken after the first plurality of moisture measurements;
        detecting at least one of a first event type and a second event type based on:
            a first determination of whether there is a drop of moisture level meeting a second predefined threshold based on the second plurality of moisture measurements; and
            a second determination of which of the first sensor and the second sensor received the first plurality and the second plurality of moisture measurements, wherein the detection is based on a weighted combination of the first determination and the second determination.

2. The method of claim 1, further comprising: automatically causing an alert based on an identified event type.

3. The method of claim 1, wherein the first event type is excretion of bodily fluid.

4. The method of claim 3, wherein the bodily fluid is urine or blood.

5. The method of claim 1, wherein the second event type is excretion of stool.

6. The method of claim 1, wherein determining whether there is the drop of moisture level meeting the second predefined threshold comprises: identifying the rise and the drop have occurred within a predefined time period.

7. The method of claim 1, wherein determining whether there is the drop of moisture level meeting the second predefined threshold comprises: calculating a rate of drop of moisture level.

8. The method of claim 1, wherein the detection is further based on a third determination of whether both of the first sensor and the second sensor detected moisture based on one or more predefined thresholds.

9. A method of monitoring a biological event associated with an individual, the method comprising:
    at a wearable device comprising:
        a puck component comprising a first moisture sensor and a second moisture sensor, and
        a strip component comprising a first circuit corresponding to the first moisture sensor and a second circuit corresponding to the second moisture sensor;
        receiving, at one of the first moisture sensor and the second moisture sensor, a first plurality of moisture measurements;
        identifying a rise of moisture level within a first predefined threshold based on the plurality of moisture measurements;
        receiving, at the same one of the first sensor and the second sensor, a second plurality of moisture measurements taken after the first plurality of moisture measurements;
        detecting at least one of a first event type and a second event type based on:
            a first determination of whether there is a drop of moisture level meeting a second predefined threshold based on the second plurality of moisture measurements;
            a second determination of which of the first sensor and the second sensor received the first plurality and the second plurality of moisture measurements; and
            a third determination of whether both of the first sensor and the second sensor detected moisture based on one or more predefined thresholds.

10. The method of claim 9, further comprising: automatically causing an alert based on an identified event type.

11. The method of claim 9, wherein the first event type is excretion of bodily fluid.

12. The method of claim 11, wherein the bodily fluid is urine or blood.

13. The method of claim 9, wherein the second event type is excretion of stool.

14. The method of claim 9, wherein determining whether there is the drop of moisture level meeting the second predefined threshold comprises: identifying the rise and the drop have occurred within a predefined time period.

15. The method of claim 9, wherein determining whether there is the drop of moisture level meeting the second predefined threshold comprises: calculating a rate of drop of moisture level.

16. The method of claim 9, wherein the detection is based on a weighted combination of the first determination and the second determination.

17. A wearable device for monitoring a biological event associated with an individual, comprising:
    a puck component comprising a first moisture sensor and a second moisture sensor, and
    a strip component comprising a first circuit corresponding to the first moisture sensor and a second circuit corresponding to the second moisture sensor;
    a memory; and
    one or more programs, wherein the one or more programs are stored in the memory and configured to be executed by the one or more processors, the one or more programs including instructions for:
        receiving, at one of the first moisture sensor and the second moisture sensor, a first plurality of moisture measurements;
        identifying a rise of moisture level within a first predefined threshold based on the plurality of moisture measurements;
        receiving, at the same one of the first sensor and the second sensor, a second plurality of moisture measurements taken after the first plurality of moisture measurements;
        detecting at least one of a first event type and a second event type based on:
            a first determination of whether there is a drop of moisture level meeting a second predefined threshold based on the second plurality of moisture measurements; and
            a second determination of which of the first sensor and the second sensor received the first plurality and the second plurality of moisture measurements, wherein the detection is based on a weighted combination of the first determination and the second determination.

18. A wearable device for monitoring a biological event associated with an individual, comprising:
   a puck component comprising a first moisture sensor and a second moisture sensor, and
   a strip component comprising a first circuit corresponding to the first moisture sensor and a second circuit corresponding to the second moisture sensor;
   a memory; and
   one or more programs, wherein the one or more programs are stored in the memory and configured to be executed by the one or more processors, the one or more programs including instructions for:
      receiving, at one of the first moisture sensor and the second moisture sensor, a first plurality of moisture measurements;
      identifying a rise of moisture level within a first predefined threshold based on the plurality of moisture measurements;
      receiving, at the same one of the first sensor and the second sensor, a second plurality of moisture measurements taken after the first plurality of moisture measurements;
      detecting at least one of a first event type and a second event type based on:
         a first determination of whether there is a drop of moisture level meeting a second predefined threshold based on the second plurality of moisture measurements; and
         a second determination of which of the first sensor and the second sensor received the first plurality and the second plurality of moisture measurements; and
         a third determination of whether both of the first sensor and the second sensor detected moisture based on one or more predefined thresholds.

\* \* \* \* \*